(12) United States Patent
Provins et al.

(10) Patent No.: US 11,155,564 B2
(45) Date of Patent: Oct. 26, 2021

(54) 2-OXO-1-IMIDAZOLIDINYL IMIDAZOTHIADIAZOLE DERIVATIVES

(71) Applicant: UCB Biopharma SRL, Brussels (BE)

(72) Inventors: Laurent Provins, Brussels (BE); Hugues Chanteux, Brussels (BE)

(73) Assignee: UCB Biopharma SRL

(*) Notice: Subject to any disclaimer, the term of this patent is extended or adjusted under 35 U.S.C. 154(b) by 0 days.

(21) Appl. No.: 16/629,774

(22) PCT Filed: Jul. 5, 2018

(86) PCT No.: PCT/EP2018/068201
§ 371 (c)(1),
(2) Date: Jan. 9, 2020

(87) PCT Pub. No.: WO2019/011767
PCT Pub. Date: Jan. 17, 2019

(65) Prior Publication Data
US 2020/0140458 A1    May 7, 2020

(30) Foreign Application Priority Data
Jul. 10, 2017   (EP) ..................................... 17180431

(51) Int. Cl.
*C07D 513/04*    (2006.01)
*A61P 25/08*    (2006.01)

(52) U.S. Cl.
CPC ............ *C07D 513/04* (2013.01); *A61P 25/08* (2018.01)

(58) Field of Classification Search
CPC .................................................... C07D 513/04
USPC .......................................................... 514/363
See application file for complete search history.

(56) References Cited

FOREIGN PATENT DOCUMENTS

WO    WO2011/047860    4/2011
WO    WO2012/143117    10/2012

*Primary Examiner* — Kahsay Habte
(74) *Attorney, Agent, or Firm* — McDonnell Boehnen Hulbert & Berghoff LLP

(57) ABSTRACT

The present invention relates to 2-oxo-1-imidazolidinyl imidazothiadiazole derivatives, processes for preparing them, pharmaceutical compositions containing them and their use as pharmaceuticals.

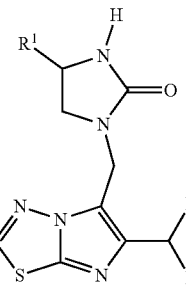

11 Claims, No Drawings

2-OXO-1-IMIDAZOLIDINYL IMIDAZOTHIADIAZOLE DERIVATIVES

CROSS-REFERENCE TO RELATED APPLICATIONS

This application is a U.S. national phase of International Application No. PCT/EP2018/068201, filed Jul. 5, 2018, which claims priority from European Patent Application EP17180431.3, filed Jul. 10, 2017, the disclosure of each of which is hereby incorporated by reference in its entirety.

INTRODUCTION

The present invention relates to 2-oxo-1-imidazolidinyl imidazothiadiazole derivatives, processes for preparing them, pharmaceutical compositions containing them and their use as pharmaceuticals.

WO2012/143117 discloses 2-oxo-1-imidazolidinyl imidazothiadiazole derivatives compounds of the following formula A:

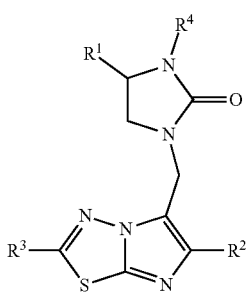

A wherein:
$R^1$ is a $C_{1-4}$ alkyl or a $C_{2-4}$ alkenyl optionally substituted by one or more (i.e. 1, 2 or 3) halogen substituents;
$R^2$ is either a halogen (chlorine, bromine, iodine) or $C_{1-4}$ alkyl containing at least one (i.e. 1, 2 or 3) halogen substituent;
$R^3$ is a $C_{1-4}$ alkyl (e.g. a methyl or an ethyl moiety) containing at least one hydroxy (OH) or an alkoxy (e.g. methoxy or ethoxy or propoxy) substituent;
$R^4$ is either hydrogen or a methyl group.

Anti-epileptic compounds of formula (I) are disclosed in WO 2011/047860: 2-oxo-1-pyrrolidinyl imidazothiadiazole derivatives according to formula (I)

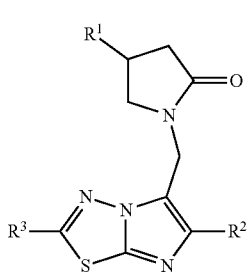

(I)

wherein
$R^1$ is a $C_{1-4}$ alkyl containing at least one halogen substituent;
$R^2$ is either a halogen (chlorine, bromine, iodine) or a $C_{1-4}$ alkyl containing at least one halogen substituent;
$R^3$ is a $C_{1-4}$ alkyl (e.g. a methyl or ethyl) containing at least one hydroxy (OH) or an alkoxy (e.g. methoxy or ethoxy or propoxy) substituent.

Anti-epileptic compounds of formula (I) are disclosed in WO 2012/143116: 4-oxo-1-imidazolidinyl imidazothiadiazole derivatives according to formula (I),

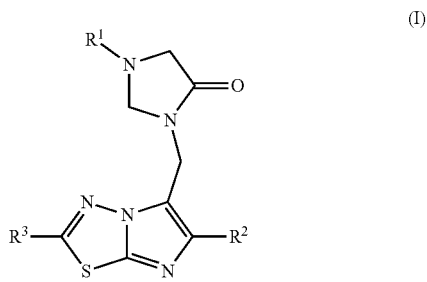

(I)

wherein
$R^1$ is a $C_{1-4}$ alkyl optionally substituted by one or more (1 to 6, preferably 2, 3 or 5) halogens, by a substituted or unsubstituted phenyl or by a substituted or unsubstituted $C_{1-4}$ cycloalkyl;
$R^2$ is either a halogen (chlorine, bromine, iodine) or a $C_{1-4}$ alkyl containing one or more (i.e. 1, 2 or 3) halogen substituents;
$R^3$ is a $C_{1-4}$ alkyl (e.g. a methyl or ethyl) containing at least one hydroxy (OH) or an alkoxy (e.g. methoxy or ethoxy or propoxy) substituent.

A persistent problem in seizure control arises with those patients who do not at all or only insufficiently respond to currently available treatments. Those patients are viewed as being refractory to treatment and represent a considerable challenge for the medical community. It is estimated that about 30% of epilepsy patients are to be classified as being refractory. Hence, there is a need to develop new medications that specifically target this population of patients.

The compounds of that invention are for use as a medicament, in the treatment of epilepsy, epileptogenesis, seizure disorders, convulsions, in particular for refractory seizures.

SUMMARY OF THE INVENTION

This invention provides new 2-oxo-1-imidazolidinyl imidazothiadiazole derivatives having the formula (I), their geometrical isomers, enantiomers, diastereoisomers, isotopes and mixtures, or a pharmaceutically acceptable salt thereof,

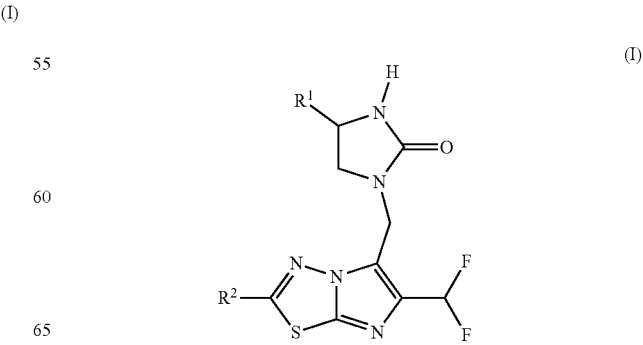

(I)

DETAILED DESCRIPTION OF THE INVENTION

The present invention relates to 2-oxo-1-imidazolidinyl imidazothiadiazole derivatives according to formula (I),

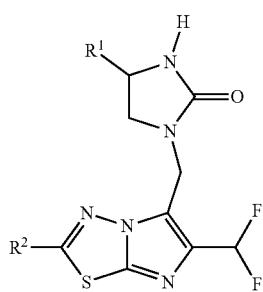

wherein
R¹ is a $C_{1-4}$ alkyl optionally substituted by one or more halogen substituents;
R² is a $C_{1-4}$ alkyl substituted by an alkoxy substituent.

Also comprised are tautomers, geometrical isomers, enantiomers, diastereomers, isotopes, and mixtures, or a pharmaceutically acceptable salt of compounds of formula (I) as well as any deuterated variant. Any hydrogen of formula (I), including any hydrogen of imidazolidinyl, can be ²H.

In a specific embodiment, R¹ is a $C_{1-4}$ alkyl optionally substituted by one or more halogen substituents.

In another specific embodiment, R¹ is an i-butyl, a n-propyl, a 2,2-difluoropropyl, a 2-chloro-2,2-difluoroethyl, a 2,2-difluoroethyl, a 2,2,2-trifluoroethyl, a 2-fluoroethyl moiety.

In another specific embodiment, R¹ is an i-butyl, a n-propyl, a 2-chloro-2,2-difluoroethyl, a 2,2,2-trifluoroethyl or a 2,2-difluoropropyl moiety.

In a preferred embodiment, R¹ is a n-propyl, 2-chloro-2,2-difluoroethyl, a 2,2-difluoropropyl or a 2,2,2-trifluoroethyl moiety.

In a more preferred embodiment, R¹ is a n-propyl or a 2,2,2-trifluoroethyl moiety.

In a further specific embodiment, R² is a methoxymethyl, a [(²H₃)methyloxy]methyl, a methoxy(²H₂)methyl, or a [(²H₃)methyloxy](²H₂)methyl moiety.

In a further specific embodiment, compounds of formula (I) are those wherein:
R¹ is a n-propyl, 2-chloro-2,2-difluoroethyl, a 2,2-difluoroethyl, a 2,2-difluoropropyl or a 2,2,2-trifluoroethyl moiety;
R² is a methoxymethyl, a [(²H₃)methyloxy]methyl, a methoxy(²H₂)methyl, or a [(²H₃)methyloxy](²H₂)methyl moiety.

In a further preferred specific embodiment, compounds of formula (I) are those wherein:
R¹ is a n-propyl or a 2,2,2-trifluoroethyl moiety;
R² is a methoxymethyl, a methoxy(²H₂)methyl, a [(²H₃)methyloxy]methyl or a [(²H₃)methyloxy](²H₂)methyl moiety.

Specific compounds of the present invention are those selected from the group consisting of:

(4S)-1-[[6-(difluoromethyl)-2-(methoxymethyl)imidazo[2,1-b][1,3,4]thiadiazol-5-yl]methyl]-4-propyl-imidazolidin-2-one;
(4R)-1-[[6-(difluoromethyl)-2-(methoxymethyl)imidazo[2,1-b][1,3,4]thiadiazol-5-yl]ethyl]-4-propyl-imidazolidin-2-one;
(+)-4-1-[[6-(difluoromethyl)-2-(methoxymethyl)imidazo[2,1-b][1,3,4]thiadiazol-5-yl]methyl]-4-(2,2,2-trifluoroethyl)imidazolidin-2-one;
(−)-4-[[6-(difluoromethyl)-2-(methoxymethyl)imidazo[2,1-b][1,3,4]thiadiazol-5-yl]methyl]-4-(2,2,2-trifluoroethyl)imidazolidin-2-one;
(4S)-1-[[2-[dideuterio(trideuteriomethoxy)methyl]-6-(difluoromethyl)imidazo[2,1-b][1,3,4]thiadiazol-5-yl]methyl]-4-propyl-imidazolidin-2-one;
(4R)-1-[[2-[dideuterio(trideuteriomethoxy)methyl]-6-(difluoromethyl)imidazo[2,1-b][1,3,4]thiadiazol-5-yl]methyl]-4-propyl-imidazolidin-2-one;
(4S)-1-[[2-[dideuterio(methoxy)methyl]-6-(difluoromethyl)imidazo[2,1-b][1,3,4]thiadiazol-5-yl]methyl]-4-propyl-imidazolidin-2-one;
(4R)-1-[[2-[dideuterio(methoxy)methyl]-6-(difluoromethyl)imidazo[2,1-b][1,3,4]thiadiazol-5-yl]methyl]-4-propyl-imidazolidin-2-one.
(−)-4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one
(+)-4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one
(+)-1-[[6-(difluoromethyl)-2-(methoxymethyl)imidazo[2,1-b][1,3,4]thiadiazol-5-yl]methyl]-4-(2,2-difluoropropyl)imidazolidin-2-one
(+)-1-[[6-(difluoromethyl)-2-(methoxymethyl)imidazo[2,1-b][1,3,4]thiadiazol-5-yl]methyl]-4-(2,2-difluoropropyl)imidazolidin-2-one
(+)-5,5-dideuterio-[[6-(difluoromethyl)-2-(methoxymethyl)imidazo[2,1-b][1,3,4]thiadiazol-5-yl]methyl]-4-propyl-imidazolidin-2-one
(+)-5,5-dideuterio-1-[[6-(difluoromethyl)-2-(methoxymethyl)imidazo[2,1-b][1,3,4]thiadiazol-5-yl]methyl]-4-propyl-imidazolidin-2-one The compounds of the present invention are for use as a medicament, in the treatment of epilepsy, epileptogenesis, seizure disorders, convulsions, in particular for refractory seizures.

The following paragraphs provide definitions of the various chemical moieties that make up the compounds according to the invention and are intended to apply uniformly throughout the specification and claims unless an otherwise expressly set out definition provides a broader definition.

"$C_{1-4}$ alkyl" refers to alkyl groups having 1 to 4 carbon atoms. This term is exemplified by groups such as methyl, ethyl, n-propyl, isopropyl, n-butyl, isobutyl, tert-butyl. "$C_{1-4}$ alkyl" groups may be substituted by one or more substituents selected from halogen, or alkoxy.

Any moiety "H" in formula (I) may be the isotope hydrogen, deuterium or tritium.

"Alkoxy" refers to the group —O—R where R includes "$C_{1-4}$ alkyl".

"Halogen" refers to fluoro, chloro, bromo and iodo atoms, preferably fluoro and chloro.

The "pharmaceutically acceptable salts" according to the invention include therapeutically active, non-toxic acid or base salt forms which the compounds of formula (I) are able to form.

The acid addition salt form of a compound of formula (I) that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula (I) containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula (I) and their salts can be in the form of a solvate, which is included within the scope of the present invention. Such solvates include for example hydrates, alcoholates and the like.

Compounds of formula (I) and/or their intermediates may have at least one stereogenic center in their structure. This stereogenic center may be present in a R or a S configuration, said R and S notation is used in correspondence with the rules described in Pure Appl. Chem., 45 (1976) 11-30. The invention thus also relates to all stereoisomeric forms such as enantiomeric and diastereoisomeric forms of the compounds of formula (I) or mixtures thereof (including all possible mixtures of stereoisomers). With respect to the present invention reference to a compound or compounds is intended to encompass that compound in each of its possible isomeric forms and mixtures thereof, unless the particular isomeric form is referred to specifically. The expression "enantiomerically pure" as used herein refers to compounds which have enantiomeric excess (ee) greater than 95%.

Compounds according to the present invention may exist in different polymorphic forms. Although not explicitly indicated in the above formula, such forms are intended to be included within the scope of the present invention.

The compounds of formula (I) according to the invention can be prepared analogously to conventional methods as understood by the person skilled in the art of synthetic organic chemistry.

According to one embodiment, compounds having the general formula (I) may be prepared by reaction of a compound of formula (II) with an urea of formula (III) according to the equation:

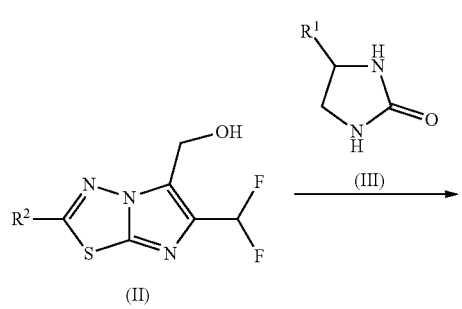

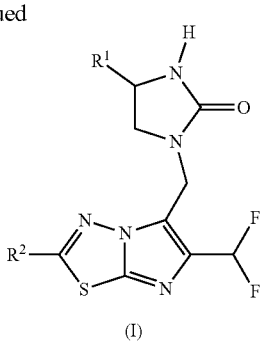

wherein $R^1$ and $R^2$ have the same definitions as defined above for compounds of formula (I).

This reaction may be performed using an acid such as p-toluenesulfonic acid in an aprotic solvent such as sulfolane at high temperature.

Compounds of formula (II) may be prepared by hydroxymethylation of a compound of formula (IV) according to the equation:

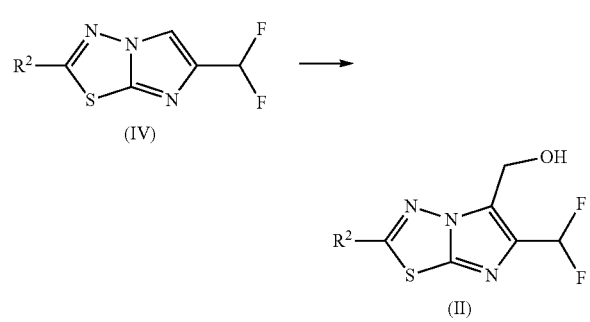

wherein $R^2$ has the same definition as defined above for compounds of formula (I).

This reaction may be performed using a formylating agent such as paraformaldehyde under acidic conditions in a polar solvent such as dioxane at 100° C., or according to any other method known to the person skilled in the art.

Compounds of formula (IV) may be synthesized by reaction of a compound of formula (V) with a bromo derivative of formula (VI) according to the equation:

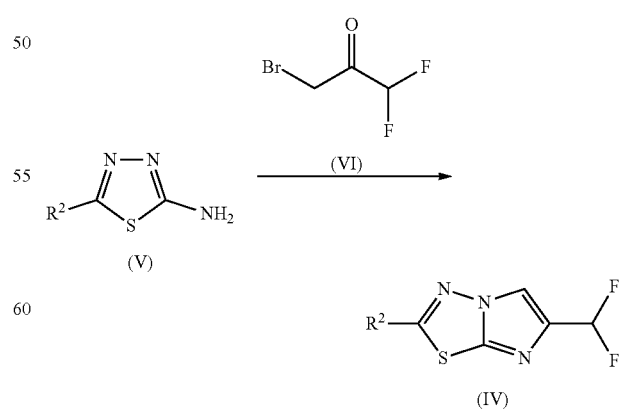

wherein $R^2$ has the same definition as described above for compounds of formula (I).

This reaction can be performed using procedures described in the literature or known to the person skilled in the art.

Compounds of formula (V) and of formula (VI) are either commercially available or may be synthesized according to any method known to the person skilled in the art.

According to one embodiment, compounds of formula (III) wherein $R^1$ is $C_{1-4}$ alkyl may be prepared by cyclization of a compound of formula (VII) according to the equation:

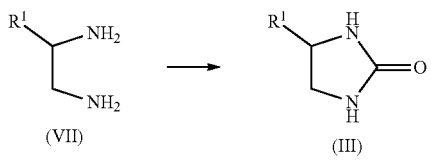

(VII) → (III)

This reaction may be performed with S,S'-dimethyl dithiocarbonate in a polar solvent such as methanol at 60° C. or using other reagents such as carbonyl diimidazole and the like or procedures known to the person skilled in the art.

Compounds of formula (VII) may be prepared by reduction of a compound of formula (VIII) according to the equation

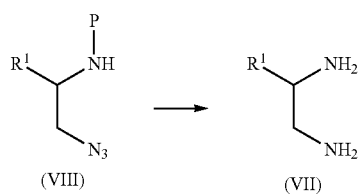

(VIII) → (VII)

wherein $R^1$ has the same definition as defined above and P is a protecting group such as benzoyl.

This reaction may be performed using a reducing agent such as, but not limited to, hydrogen in the presence of a catalyst such as palladium on charcoal in a polar solvent such as methanol or by other procedures known to the person skilled in the art.

Compounds of formula (VIII) may be prepared starting from commercially available amino acids wherein $R^1$ has the same definition as defined above according to any reaction sequence known to the person skilled in the art. Alternatively, compounds of formula (VIII) may be prepared by a sequence of reactions starting from commercially available esters or aldehydes and subsequent formation of intermediate amino-alcohols according to any procedures known to the person skilled in the art.

According to another embodiment, compounds of formula (III) wherein $R^1$ is 2,2,2-trifluoroethyl may be prepared by deprotection of a compound of formula (IX) wherein P is a protecting group such as benzyl according to the equation:

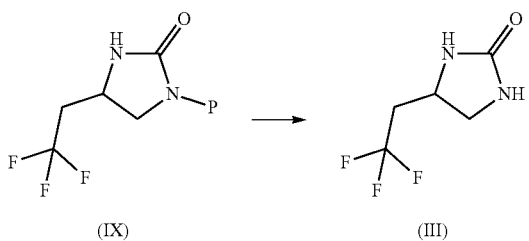

(IX) → (III)

This reaction may be performed according to any method known to the person skilled in the art.

Compounds of formula (IX) may be prepared by cyclization of a compound of formula (X) wherein R is an alkyl group according to the equation:

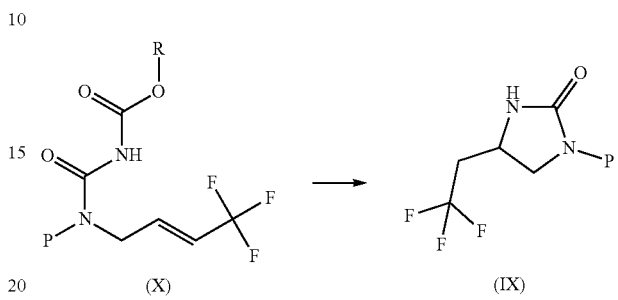

(X) → (IX)

This reaction may be performed in the presence of a base such as sodium hydroxide in a protic polar solvent such as 2,2,2-trifluoroethanol at reflux temperature.

Compounds of formula (X) may be prepared starting from a compound of formula (XI) and an isocyanate of formula (XII) according to the equation:

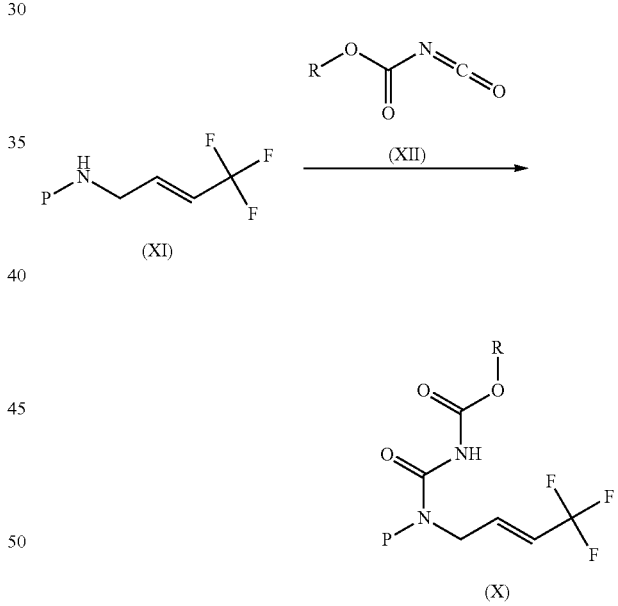

(XI) + (XII) → (X)

This reaction may be performed in a polar solvent such as methyl-THF at 0° C. or according to any method known to the person skilled in the art.

Compounds of formula (XI) may be prepared starting from the commercially available corresponding alcohol according to any reaction sequence known to the person skilled in the art.

According to another embodiment, compounds of formula (III) wherein $R^1$ is 2-chloro-2,2-difluoroethyl may be prepared by deprotection of a compound of formula (XII) wherein P is a protecting group such as benzyl according to the equation:

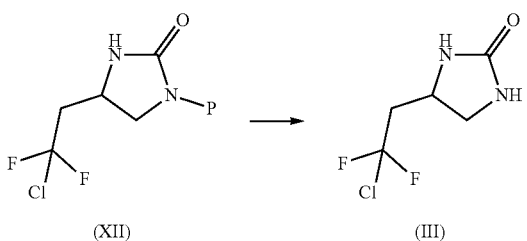

(XII)                                    (III)

This reaction may be performed according to any method known to the person skilled in the art.

Compounds of formula (XII) may be prepared by chlorination and decarboxylation of a compound of formula (XIII) wherein R is an alkyl group, according to the equation:

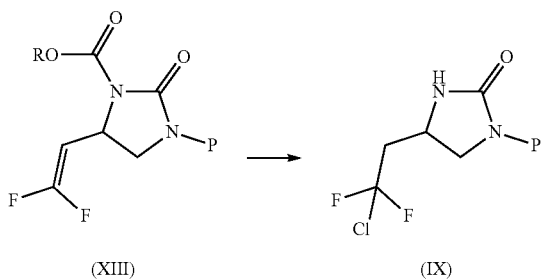

(XIII)                                   (IX)

This reaction may be performed using an excess of hydrochloric acid in acetic acid at reflux temperature.

Compounds of formula (XIII) may be prepared by cyclisation of a compound of formula (X) according to the equation:

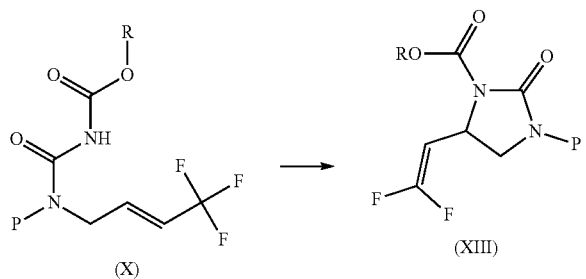

(X)                                      (XIII)

This reaction may be performed in the presence of a base such as potassium tert-butoxide in a non-protic polar solvent such ad N,N-dimethylformamide at a temperature ranging from 70 to 90° C.

The compounds of the present invention are for use as a medicament, in the treatment of epilepsy, epileptogenesis, seizure disorders, convulsions, in particular for refractory seizures.

Seizures can be classified as refractory when a patient fails to achieve seizure freedom for 12 months or more of state of the art treatment with two or more anti-epileptic drugs at maximal tolerated doses. The International League Against Epilepsy (ILAE) has defined drug resistant epilepsy as "failure of adequate trials of two tolerated and appropriately chosen and used AED schedules (whether as monotherapies or in combination) to achieve sustained seizure freedom".

The methods of the invention comprise administration to a mammal (preferably a human) suffering from above mentioned conditions or disorders, of a compound according to the invention in an amount sufficient to alleviate or prevent the disorder or condition.

The compound is conveniently administered in any suitable unit dosage form, including but not limited to one containing 1 to 2000 mg, preferably 1 to 1000 mg, more preferably 1 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a chronic neurologic condition characterised by unprovoked, recurrent epileptic seizures. An epileptic seizure is the manisfestation of an abnormal and excessive synchronised discharge of a set of cerebral neurons; its clinical manifestations are sudden and transient. The term "epilepsy" as used herein can also refer to a disorder of brain function characterised by the periodic occurrence of seizures. Seizures can be "nonepileptic" when evoked in a normal brain by conditions such as high fever or exposure to toxins or "epileptic" when evoked without evident provocation.

The term "seizure" as used herein refers to a transient alteration of behaviour due to the disordered, synchronous, and rhythmic firing of populations of brain neurones.

A further aspect of the present invention relates to a pharmaceutical composition comprising an effective amount of a compound of formula (I) in combination with a pharmaceutically acceptable diluent or carrier.

Activity in any of the above-mentioned indications can of course be determined by carrying out suitable clinical trials in a manner known to a person skilled in the relevant art for the particular indication and/or in the design of clinical trials in general.

For treating diseases, compounds of formula (I) or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula (I) or a pharmaceutically acceptable salt thereof in combination with a pharmaceutically acceptable diluent or carrier.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, transdermally (patch), by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner.

Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration.

Thus the quantity of compound of formula (I) in compositions for oral administration is at least 0.5% by weight and can be up to 80% by weight with respect to the total weight of the composition.

In accordance with the invention it has also been found that the compounds of formula (I) or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenytoin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives and amantadine.

For oral compositions, the daily dosage is in the range 1 mg to 2000 mg of compounds of formula (I). Preferably in the range 1 mg to 1000 mg of compounds of formula (I), most preferably 1 mg to 500 mg.

In compositions for parenteral administration, the quantity of compound of formula (I) present is at least 0.5% by weight and can be up to 33% by weight with respect to the total weight of the composition. For the preferred parenteral compositions, the dosage unit is in the range 1 mg to 2000 mg of compounds of formula (I).

The daily dose can fall within a wide range of dosage units of compound of formula (I) and is generally in the range 1 to 2000 mg, preferably 1 to 1000 mg. However, it should be understood that the specific doses can be adapted to particular cases depending on the individual requirements, at the physician's discretion.

The SV2 proteins binding compounds provided by this invention and labeled derivatives thereof may be useful as standards and reagents in determining the ability of tested compounds (e.g., a potential pharmaceutical) to bind to the SV2 proteins.

Labeled derivatives of SV2 proteins' ligands provided by this invention may also be useful as radiotracers for positron emission tomography (PET) imaging or for single photon emission computerized tomography (SPECT).

The present invention therefore further provides labelled ligands as tools to screen chemical libraries for the discovery of potential pharmaceutical agents, in particular for treatment and prevention of the conditions set forth herein, on the basis of more potent binding to SV2 proteins, for localizing SV2 proteins in tissues, and for characterizing purified SV2 proteins. SV2 proteins include SV2A, SV2B, and SV2C whereby SV2A is the binding site for the anti-seizure drug levetiracetam and its analogs. The SV2 isoforms SV2A, SV2B, or SV2C can be derived from tissues, especially brain, from any mammal species, including human, rat or mice. Alternately the isoforms may be cloned versions of any mammalian species, including human, rat, and mice, heterologously expressed and used for assays. The screening method comprises exposing brain membranes, such as mammalian or human brain membranes, or cell lines expressing SV2 proteins or fragments thereof, especially SV2A and SV2C, but including SV2B, to a putative agent and incubating the membranes or proteins or fragments and the agent with labelled compound of formula (I). The method further comprises determining if the binding of the compound of formula (I) to the protein is inhibited by the putative agent, thereby identifying binding partners for the protein. Thus, the screening assays enable the identification of new drugs or compounds that interact with SV2 proteins. The present invention also provides photoactivable ligands of SV2 proteins.

The labelled-ligands can also be used as tools to assess the conformation state of SV2 proteins after solubilization, purification and chromatography. The labelled-ligands may be directly or indirectly labeled. Examples of suitable labels include a radiolabel, such as $^3H$, a fluorescent label, an enzyme, europium, biotin and other conventional labels for assays of this type.

Labelled compounds of formula (I) are useful in the methods as probes in assays to screen for new compounds or agents that bind to the SV2 proteins (SV2A, SV2B and SV2C). In such assay embodiments, ligands can be used without modification or can be modified in a variety of ways; for example, by labelling, such as covalently or non-covalently joining a moiety which directly or indirectly provides a detectable signal. In any of these assays, the materials can be labelled either directly or indirectly.

Possibilities for direct labelling include label groups such as: radiolabels including, but not limited to, $[^3H]$, $[^{14}C]$, $[^{32}P]$, $[^{35}S]$ or $[^{125}I]$, enzymes such as peroxidase and alkaline phosphatase, and fluorescent labels capable of monitoring the change in fluorescence intensity, wavelength shift, or fluorescence polarization, including, but not limited to, fluorescein or rhodamine. Possibilities for indirect labelling include biotinylation of one constituent followed by binding to avidin coupled to one of the above label groups or the use of anti-ligand antibodies. The compounds may also include spacers or linkers in cases where the compounds are to be attached to a solid support. To identify agents or compounds which compete or interact with labelled ligands according to the invention for binding to the SV2 proteins (especially SV2A and SV2C), intact cells, cellular or membrane fragments containing SV2A or SV2C or the entire SV2 protein or a fragment thereof can be used. The agent or compound may be incubated with the cells, membranes, SV2 protein or fragment prior to, at the same time as, or after incubation with labelled levetiracetam or an analog or derivative thereof. Assays may be modified or prepared in any available format, including high-throughput screening (HTS) assays that monitor the binding of levetiracetam or the binding of derivatives or analogs thereof to SV2 proteins or fragments thereof. In many drug screening programs which test libraries of compounds, high throughput assays are desirable in order to maximize the number of compounds surveyed in a given period of time. Such screening assays may use intact cells, cellular or membrane fragments containing SV2 as well as cell-free or membrane-free systems, such as may be derived with purified or semi-purified proteins. The advantage of the assay with membrane fragment containing SV2 or purified SV2 proteins and peptides is that the effects of cellular toxicity and/or bioavailability of the test compound can be generally ignored, the assay instead being focused primarily on the effect of the drug on the molecular target as may be manifest in an inhibition of, for instance, binding between two molecules. The assay can be formulated to detect the ability of a test agent or compound to inhibit binding of labeled ligand according to the invention to SV2 or a fragment of SV2 or of labelled levetiracetam, or derivatives or analogs thereof, to SV2 or a fragment of SV2 protein. The inhibition of complex formation may be detected by a variety of techniques such as filtration assays, Flashplates (Perkin Elmer), scintillation proximity assays (SPA, GE). For high-throughput screenings (HTS), scintillation proximity assay which uses microspheres coated with biological membranes or flashplates coated with biological membranes are powerful methods that do not require separation or washing steps.

A problem which can be faced when developing compounds for use in therapy is the capacity of certain compounds (perpetrator drugs), which could be co-administered together with the compounds of the present invention (victim drugs), to induce CYP450 enzymes, in particular CYP3A4/5. The induction of such enzymes by the perpetrator drugs may impact the exposure of the victim drug, when mainly metabolized by CYP450 enzymes and CYP3A4/5 in particular, thereby potentially altering their efficacy profile. It is therefore desirable to develop compounds with limited potential for metabolization by CYP3A4/5 enzymes.

The CYP3A4/5 contribution to the total metabolism of compounds according to the present invention has been evaluated by calculating the ratio between human hepatocytes clearances in absence and presence of a selective CYP3A4/5 inhibitor such as azamulin.

When tested in this assay according to the protocol described in the present patent application, compounds according to the present invention exhibit a fraction metabolized by CYP3A4/5 ($F_{m,CYP3A4/5}$) typically lower than 40%, therefore minimizing the risk for drug-drug interactions when coadministered with CYP450 inducers.

In addition, it may be beneficial that the compounds according to the present invention demonstrate low intrinsic clearances.

EXPERIMENTAL SECTION

Abbreviations/Recurrent Reagents

Ac: acetyl
ACN: Acetonitrile
Brine: Saturated aqueous sodium chloride solution
nBu: n-butyl
tBu: tert-butyl
Bz: benzoyl
CV: column volumes
DCM: Dichloromethane
DMF: N,N-Dimethylformamide
DMSO: Dimethylsulfoxide
Et: Ethyl
EtOH: Ethanol
$Et_2O$: Diethyl ether
EtOAc: Ethyl acetate
h: Hour
HPLC: High Pressure Liquid Chromatography
LC: Liquid Chromatography
LCMS: Liquid Chromatography Mass Spectrometry
MeOH: Methanol
min.: minutes
NMR: Nuclear magnetic resonance
iPrOH: isopropanol
PTSA: p-toluenesulfonic acid
RT: room temperature
SFC: Supercritical Fluid Chromatography
THF: Tetrahydrofuran
TLC: Thin Layer Chromatography Analytical Methods All reactions involving air or moisture-sensitive reagents were performed under a nitrogen or argon atmosphere using dried solvents and glassware. Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling). Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography, HPLC or mass spectrometry analyses.

HPLC analyses are performed using an Agilent 1100 series HPLC system mounted with a Waters XBridge MS C18, 5 pm, 150×4.6 mm column. The gradient runs from 100% solvent A (water/ACN/ammonium formate solution 85/5/10 (v/v/v)) to 100% solvent B (water/ACN/ammonium formate solution 5/85/10 (v/v/v) in 6 min. with a hold at 100% B of 5 minutes. The flow rate is set at 8 mL/min during 6 min. then increased at 3 mL/min during 2 min. with a hold at 3 mL/min during 3 minutes. A split of ⅕ is used just before API source. The chromatography is carried out at 45° C. The ammonium formate solution (pH-8.5) is prepared by dissolution of ammonium formate (630 mg) in water (1 L) and addition of ammonium hydroxide 30% (500 μL).

It will be apparent to the one skilled in the art that different retention times may be obtained for LC data if different analytical conditions are used.

Mass spectrometric measurements in LCMS mode are performed as follows:

For Basic Elution, Analyses are Performed Using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an basic elution. The reverse phase separation is carried out at 45° C. on a Waters Acquity UPLC BEHC18 1.7 μm (2.1×50 mm) column for basic elution. Gradient elution is done with water/ACN/ammonium formate (95/5/63 mg/L) (solvent A) and ACN/water/ammonium formate (95/5/63 mg/L) (solvent B). Injection volume: 1 μL. Full flow in MS.

| Basic program "4 min" | | | |
|---|---|---|---|
| Time (min) | A (%) | B (%) | Flow (mL/min) |
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |

| Basic program "10 min" | | | |
|---|---|---|---|
| Time (min) | A (%) | B (%) | Flow (mL/min) |
| 0 | 99 | 1 | 0.4 |
| 0.8 | 99 | 1 | 0.4 |
| 5.3 | 0 | 100 | 0.4 |
| 5.35 | 0 | 100 | 0.5 |
| 7.30 | 0 | 100 | 0.5 |

For Acidic Elution, Analyses are Performed Using:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive mode with an acidic elution. The reverse phase separation is carried out at 45° C. on a Waters Acquity UPLC HSS T3 1.8 μm (2.1×50 mm) column for acidic elution. Gradient elution is done with water/ACN/TFA (95/5/0.5 mL/L) (solvent A) and ACN (solvent B). Injection volume: 1 μL. Full flow in MS.

| Acidic program "4 min" | | | |
|---|---|---|---|
| Time (min) | A (%) | B (%) | Flow (mL/min) |
| 0 | 99 | 1 | 0.4 |
| 0.3 | 99 | 1 | 0.4 |
| 3.2 | 5 | 95 | 0.4 |
| 3.25 | 5 | 95 | 0.5 |
| 4 | 5 | 95 | 0.5 |

| Acidic program "10 min" | | | |
|---|---|---|---|
| Time (min) | A (%) | B (%) | Flow (mL/min) |
| 0 | 99 | 1 | 0.4 |
| 0.8 | 99 | 1 | 0.4 |
| 5.3 | 5 | 95 | 0.4 |
| 5.35 | 5 | 95 | 0.5 |
| 7.30 | 5 | 95 | 0.5 |

Crude materials could be purified by normal phase chromatography, (acidic or basic) reverse phase chromatography, chiral separation or recrystallization.

Normal reverse phase chromatography are performed using silica gel columns (100:200 mesh silica gel or Puriflash®-50SIHC-JP columns from Interchim).

Preparative Reverse Phase Chromatography are Performed as Follows:

LCMS purification (Basic mode, LCMS prep) using a SQD or QM Waters triple quadrupole mass spectrometer is used for LCMS purification. This spectrometer is equipped with an ESI source and a Prep LC controller Waters quaternary pump with diode array detector (210 to 400 nm).

Ms Parameters:

ESI capillary voltage 3 kV. Cone and Extractor voltage 10. Source block temperature 120° C. Desolvation temperature 300° C. Cone gaz flow 30 L/h (Nitrogen), Desolvation Gas flow 650 L/h. Data are acquired in a full MS scan from m/z 100 to 700 in positive mode with an acidic or a basic elution.

LC Parameters:

The reverse phase separation is carried out at rt on a XBridge prep OBD C18 column (5 μm, 30×50 mm) (basic elution). Gradient elution is done with Water (solvent A), ACN (solvent B), Ammonium bicarbonate in water 8 g/L+ 500 μL/L NH$_4$OH 30% (solvent C) (pH~8.5). HPLC flow rate: 35 mL/min to 60 mL/min, injection volume: 1 mL. The splitting ratio is set at +/−1/6000 to MS.

| Time (min) | A (%) | B (%) | C (%) | Flow (mL/min) |
|---|---|---|---|---|
| 0 | 85 | 5 | 10 | 35 |
| 1 | 85 | 5 | 10 | 35 |
| 7 | 5 | 85 | 10 | 35 |
| 9 | 5 | 95 | 0 | 60 |
| 12 | 5 | 95 | 0 | 60 |
| 12.5 | 85 | 5 | 10 | 35 |
| 16 | 85 | 5 | 10 | 35 |

Preparative Chiral Chromatographic separations are performed on using liquid phase chromatography or supercritical fluid chromatography (SFC) instruments with various mixtures of lower alcohols and $C_5$ to $C_8$ linear, branched or cyclic alkanes at 360 mL/min. Solvent mixtures as well as columns are described in individual procedures.

Products were generally dried under vacuum before final analyses and submission to biological testing.

NMR spectra are recorded on a BRUKER AVANCEIII 400 MHz-Ultrashield NMR Spectrometer fitted with a Windows 7 Professional workstation running Topspin 3.2 software and a 5 mm Double Resonance Broadband Probe (PABBI 1H/19F-BB Z-GRD Z82021/0075) or a 1 mm Triple Resonance Probe (PATXI 1H/D-13C/15N Z-GRD Z868301/004). The compounds were studied in DMSO-$d_6$, or CDCl$_3$ solution at a probe temperature of 300 K and at a concentration of 10 mg/mL. The instrument is locked on the deuterium signal of DMSO-$d_6$, or $CDCl_3$. Chemical shifts are given in ppm downfield from TMS (tetramethylsilane) taken as internal standard.

Optical rotations ($[\alpha]_D$) were measured on a PERKIN-ELMER polarimeter 341 in a cuvette (1=1 dm) at a 10 mg/mL concentration, at a temperature mentioned in the specific examples, at 589 nm (sodium lamp).

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Example 1. Synthesis of (4S)-1-[[6-(difluoromethyl)-2-(methoxymethyl)imidazo[2,1-b][1,3,4]thiadiazol-5-yl]methyl]-4-propyl-imidazolidin-2-one 1 and the mixture was stirred at 75° C. for 16 h. The methanol was evaporated to dryness to give a colorless oil which was solubilized in ethyl acetate. The organic layer was washed with water and brine, then dried over $MgSO_4$, filtered and evaporated to dryness to give methyl (2S)-2-(benzyloxycarbonylamino)pentanoate I (10.41 g, 39.24 mmol) as a colorless oil (containing impurities). The crude was used in the next step without any further purification.

Estimated Yield: Quantitative

LC/MS: $[M+H]^+=266.3$ $^1H$ NMR (400 MHz, DMSO-$d_6$): δ 7.45-7.12 (m, 5H), 5.04 (s, 2H), 4.11-3.93 (m, 1H), 3.63 (s, 3H), 2.50 (p, J=1.8 Hz, 1H), 1.79-1.47 (m, 2H), 1.45-1.22 (m, 2H), 0.86 (t, J=7.4 Hz, 3H).

Methyl (2R)-2-(benzyloxycarbonylamino)pentanoate IA is prepared according to the same procedure starting from N-α-benzyloxycarbonyl-D-norvaline (CAS: 42918-89-8). Estimated yield: quantitative.

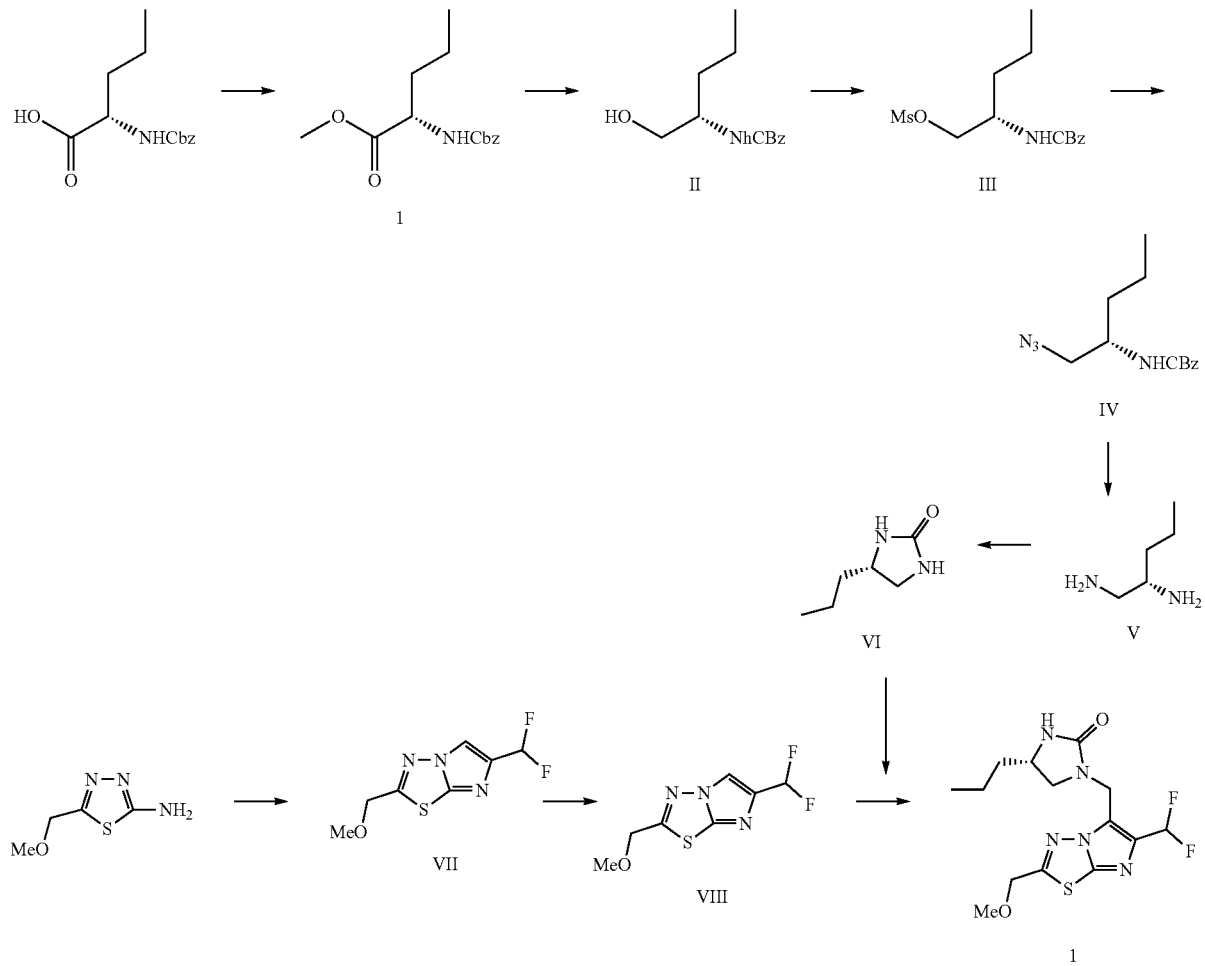

1.1 Synthesis of methyl (2S)-2-(benzyloxycarbonylamino)pentanoate I

To a solution of N-α-benzyloxycarbonyl-L-norvaline (CAS: 21691-44-1, 1.0 eq., 10 g, 38.60 mmol) in methanol (400 mL) was added sulfuric acid (0.05 eq., 0.1 mL, 2 mmol)

1.2 Synthesis of benzyl N-[(1S)-1-(hydroxymethyl)butyl] carbamate II

To a mixture of methyl (2S)-2-(benzyloxycarbonylamino)pentanoate I (1.0 eq., 48 g, 180.9 mmol) in ethanol (1 L), at −10° C., was slowly added sodium borohydride (1.05 eq., 7.2 g, 190 mmol). The mixture was allowed to warm up to room temperature and stirred for 24 h. The mixture was cooled to 0° C. and an aqueous saturated solution of NaHCO$_3$ was slowly added. The aqueous layer was extracted with ethyl acetate. The combined organic layers were washed with brine, dried over MgSO$_4$, filtered and evaporated to dryness to give a colorless oil (83 g). The crude was purified by preparative LC (SiO$_2$ 10 μm, diam 8 cm, 1.2 kg, CH$_2$Cl$_2$/MeOH/NH$_4$OH gradient from 99/0.9/0.1 to 95/4.5/0.5) to give benzyl N-[(1S)-1-(hydroxymethyl) butyl] carbamate (26 g, 103.1 mmol) II as a white solid.

Yield: 57%

LC/MS: [M+H]$^+$=238.3

$^1$H NMR (400 MHz, DMSO-d$_6$): δ 7.33 (tdd, J=8.6, 5.7, 2.1 Hz, 5H), 6.91 (d, J=8.6 Hz, 1H), 4.99 (s, 2H), 4.57 (t, J=5.6 Hz, 1H), 3.42 (dp, J=13.9, 5.3, 4.9 Hz, 1H), 3.29-3.17 (m, 1H), 1.49-1.17 (m, 4H), 0.84 (t, J=6.9 Hz, 3H).

Benzyl N-[(1R)-1-(hydroxymethyl)butyl] carbamate IIA is prepared according to the same procedure starting from Methyl (2R)-2-(benzyloxycarbonylamino)pentanoate IA.

Yield: 60%.

1.3 Synthesis of benzyl [(2S)-2-(benzyloxycarbonylamino)pentyl] methanesulfonate III To a mixture of benzyl N-[(1S)-1-(hydroxymethyl)butyl] carbamate II (1.0 eq., 31.2 g, 131 mmol) and triethylamine (1.1 eq., 20.4 mL, 145 mmol) in dichloromethane (1 L) at 0° C. was added methanesulfonyl chloride (1.1 eq., 11.2 mL, 145 mmol). The reaction was allowed to warm up to room temperature and stirred for 32 h. The crude mixture was washed with water (two times) and then brine. The organic layer was dried over MgSO$_4$, filtered and evaporated to dryness to give a yellow solid (41 g) which was purified by preparative LC (SiO$_2$ 10 μm, diam 8 cm, 1.2 kg, CH$_2$Cl$_2$/MeOH/NH$_4$OH gradient from 100/0/0 to 95/4.5/0.5). The pure fractions were evaporated to dryness to give [(2S)-2-(benzyloxycarbonylamino)pentyl] methanesulfonate III (25.7 g, 81.5 mmol) as yellow solid.

Yield: 62%

LC/MS: [M+H]$^+$=316.4

$^1$H NMR (400 MHz, DMSO-d$_6$): δ 7.44-7.26 (m, 5H), 5.05 (s, 2H), 4.32-4.01 (m, 3H), 3.75 (d, J=5.7 Hz, 1H), 3.15 (s, 3H), 1.52-1.30 (m, 4H), 0.87 (t, J=7.1 Hz, 3H).

Benzyl [(2R)-2-(benzyloxycarbonylamino)pentyl] methanesulfonate IIIA is prepared according to the same procedure starting from benzyl N-[(1R)-1-(hydroxymethyl)butyl] carbamate IIA. Yield: 43%

1.4 Synthesis of Benzyl N-[(1S)-1-(azidomethyl)butyl]carbamate IV

To a mixture of [(2S)-2-(benzyloxycarbonylamino)pentyl] methanesulfonate III (1.0 eq., 2.3 g, 7.3 mmol) in DMF (50 mL), sodium azide (1.1 eq., 520 mg, 7.9 mmol) was added and the mixture was stirred at 80° C. for 5 h. The reaction mixture was diluted with ethyl acetate and the organic layer was washed with water (three times) and brine (two times), dried over MgSO$_4$, filtered and evaporated to dryness to give benzyl N-[(1S)-1-(azidomethyl)butyl]carbamate IV (1.18 g, 4.0 mmol, 90% purity) a yellow oil. The product was used in the next step without any further purification.

Estimated Yield: 56%

LC/MS: [M+H]$^+$=263.3

$^1$H NMR (400 MHz, DMSO-d6): δ 7.39-7.27 (m, 5H), 5.04 (s, 2H), 3.69-3.54 (m, 1H), 3.28 (dd, J=10.3, 6.1 Hz, 2H), 1.32 (m, 4H), 0.85 (t, J=7.1 Hz, 3H).

Benzyl N-[(1R)-1-(azidomethyl)butyl]carbamate IVA is prepared according to the same procedure starting from benzyl [(2R)-2-(benzyloxycarbonylamino)pentyl] methanesulfonate IIIA. Yield: 60%

1.5 Synthesis of (2S)-pentane-1,2-diamine V

To a solution of benzyl N-[(1S)-1-(azidomethyl) butyl] carbamate IV (1.0 eq., 4.7 g, 17.8 mmol) in methanol (200 mL), at room temperature under argon atmosphere, was added Pd/C (5% w/w, 230 mg, 2.2 mmol). The mixture was then hydrogenated at room temperature under H$_2$ pressure (1 atm) in a Parr® pressure vessel reactor for 24 h. The crude mixture was filtered over Celite and the filtrate was evaporated to dryness to give (2S)-pentane-1,2-diamine V (2.0 g, 19.5 mmol) as a yellow oil which was directly used in the next step without any further purification.

Yield: Quantitative

LC/MS: No ionization $^1$H NMR (400 MHz, DMSO-d$_6$): δ 2.46 (dt, J=11.6, 3.5 Hz, 1H), 2.22 (dd, J=11.7, 6.9 Hz, 1H), 1.45-1.20 (m, 3H), 1.19-0.99 (m, 1H), 0.86 (t, J=7.1 Hz, 3H).

(2R)-pentane-1,2-diamine VA is prepared according to the same procedure starting from benzyl N-[(1R)-1-(azidomethyl)butyl]carbamate IVA. Yield: 78%

1.6 Synthesis of (4S)-4-propylimidazolidin-2-one VI

To a solution of (2S)-pentane-1,2-diamine V (1.0 eq., 16.5 g, 161 mmol) in methanol (160 mL) at room temperature was added S,S'-dimethyl dithiocarbonate (1.0 eq., 20.3 g, 161 mmol) and the mixture was stirred overnight at 60° C. The crude reaction was concentrated to dryness to give a yellow solid which was triturated in diethyl ether. The obtained precipitate was filtered, washed with diethyl ether (three times) and dried under vacuum to give (4S)-4-propylimidazolidin-2-one VI (6.99 g, 54.5 mmol) as a white solid.

Yield: 34%

LC/MS: [M+H]$^+$=129.17

$^1$H NMR (400 MHz, DMSO-d$_6$): δ 6.35 (s, 1H), 6.03 (s, 1H), 3.63-3.47 (m, 1H), 3.39 (s, 1H), 2.87 (ddd, J=8.4, 6.9, 1.3 Hz, 1H), 1.48-1.15 (m, 4H), 0.87 (t, J=7.1 Hz, 3H).

(4R)-4-propylimidazolidin-2-one VIA is prepared according to the same procedure starting from (2R)-pentane-1,2-diamine VA. Yield: 64%

1.7 Synthesis of 6-(difluoromethyl)-2-(methoxymethyl)imidazo[2,1-b][1,3,4]thiadiazole VII To a solution of 5-(methoxymethyl)-1,3,4-thiadiazol-2-amine (CAS: 15884-86-3, 1.0 eq., 6.5 g, 45 mmol) in DMF (100 mL), at 100° C., was added dropwise a solution of 3-bromo-1,1-difluoro-propan-2-one (CAS: 883233-85-0, 1.05 eq., 8.1 g, 47 mmol) in DMF (5 mL). The reaction mixture was heated at 100° C. during 3 h and the completion was checked by LC/MS. A saturated aqueous solution of NaHCO$_3$ was added and the organic layer was extracted with ethyl acetate (three times). The combined organic layers were washed with water (five times), dried over MgSO$_4$, filtered and evaporated to dryness to give a brown solid (7.6 g). The crude was purified by flash chromatography Biotage Isolera Four (100 g KP-SNAP silica gel column in a gradient of 0% to 5% methanol in dichloromethane over 12 CV) and the pure fractions were combined and evaporated under high vacuum to give 6-(difluoromethyl)-2-(methoxymethyl)imidazo[2,1-b][1,3,4]thiadiazole VII (3.95 g, 17.8 mmol) as an orange solid.

Yield: 40%

LC/MS: [M+H]$^+$=220.2

$^1$H NMR (400 MHz, DMSO-d$_6$): δ 8.53 (t, J=2.2 Hz, 1H), 7.01 (t, J=54.6 Hz, 1H), 4.83 (s, 2H), 3.43 (s, 3H).

1.8 Synthesis of [6-(difluoromethyl)-2-(methoxymethyl)imidazo[2,1-b][1,3,4]thiadiazol-5-yl]methanol VIII In a sealed tube, 6-(difluoromethyl)-2-(methoxymethyl) imidazo[2,1-b][1,3,4]thiadiazole VII (1.0 eq., 3.95 g, 18.0 mmol), paraformaldehyde (6.0 eq., 3.24 g, 108 mmol,) and an aqueous solution of hydrochloric acid (2N) (0.9 equiv., 8.1 mL, 16.2 mmol) were mixed in 1,4-dioxane (8 mL). The mixture was stirred at 100° C. for 3.5 h and the reaction was checked by LC/MS. The crude mixture was warmed to RT and an aqueous saturated solution of NaHCO$_3$ was added until pH=6-7. The aqueous layer was extracted with ethyl acetate (three times) and the combined organic layers were washed with brine, dried over MgSO$_4$, filtered and evaporated to dryness. The crude was purified by flash chromatography Biotage Isolera Four (100 g KP-SNAP silica gel column in a gradient of 0% to 10% methanol in dichloromethane over 15 CV) to give a yellow oil (3 g) which was purified a second time by reverse phase HPLC (KROMASIL-Eternity XT C$_{18}$ 10 μm/ACN/H$_2$O/NH$_4$OH gradient from 20/80/0.1 to 50/50/0.1). The purest fractions were evaporated to dryness to give [6-(difluoromethyl)-2-(methoxymethyl)imidazo[2,1-b][1,3,4]thiadiazol-5-yl] methanol VIII (2 g, 8.02 mmol) as a white solid.

Yield: 45%

LC/MS: [M+H]$^+$=250.2

$^1$H NMR (400 MHz, DMSO-d$_6$): δ 7.11 (t, J=53.6 Hz, 1H), 5.47 (t, J=5.4 Hz, 1H), 4.84 (s, 2H), 4.79 (d, J=5.5 Hz, 2H), 3.44 (d, J=0.9 Hz, 3H).

1.9 Synthesis of (4S)-1-[[6-(difluoromethyl)-2-(methoxymethyl)imidazo[2,1-b][1,3,4]thiadiazol-5-yl]methyl]-4-propyl-imidazolidin-2-one 1

To a mixture of [6-(difluoromethyl)-2-(methoxymethyl) imidazo[2,1-b][1,3,4]thiadiazol-5-yl]methanol VIII (1.0 eq., 1.5 g, 6.0 mmol) and (4S)-4-propylimidazolidin-2-one VI (1.8 eq., 1.4 g, 11 mmol) in sulfolane (30 mL), was added p-toluenesulfonic acid monohydrate (1.0 eq., 1.1 g, 5.8 mmol) and the mixture was stirred at 110° C. for 3.5 h. The mixture was cooled to room temperature, diluted with methyl tert-butyl ether and water. The aqueous layer was extracted with methyl tert-butyl ether (three times). The combined organic layer were washed with an aqueous solution of HCl (1N), water (two times) and evaporated to dryness to give a brown solid (1.3 g). The crude was purified by reverse phase preparative HPLC (KROMASIL-Eternity XT C$_{18}$ 10 μm/ACN/H$_2$O/NH$_4$OH gradient from 30/70/0.1 to 60/40/0.1) to give a beige solid (923 mg of the mixture of regioisomers) which was purified by achiral SFC (silica beta 22×250 mm, CO$_2$/EtOH co-solvent 10%/150 bars/360 mL/min). The purest fractions were evaporated to dryness to give (4S)-1-[[6-(difluoromethyl)-2-(methoxymethyl)imidazo[2,1-b][1,3,4]thiadiazol-5-yl]methyl]-4-propyl-imidazolidin-2-one 1 (315 mg, 0.87 mmol) as a beige solid.

Yield: 15%

LC/MS: [M+H]$^+$=360.4

$^1$H NMR (400 MHz, CDCl$_3$): δ 6.85 (t, J=54.5 Hz, 1H), 4.89-4.63 (m, 4H), 4.53 (s, 1H), 3.60 (dtd, J=8.2, 6.6, 1.4 Hz, 1H), 3.48 (d, J=22.2 Hz, 4H), 2.96 (dd, J=8.6, 6.8 Hz, 1H), 1.56-1.37 (m, 2H), 1.29 (ddt, J=13.9, 6.9, 5.2 Hz, 2H), 0.91 (t, J=7.3 Hz, 3H).

(4R)-1-[[6-(difluoromethyl)-2-(methoxymethyl)imidazo [2,1-b][1,3,4]thiadiazol-5-yl]methyl]-4-propyl-imidazolidin-2-one 2 is prepared according to the same procedure starting from (4R)-4-propylimidazolidin-2-one VIA. Yield: 26%

Example 2. Synthesis of (+)-1-[[6-(difluoromethyl)-2-(methoxymethyl)imidazo[2,1-b][1,3,4]thiadiazol-5-yl]methyl]-4-(2,2,2-trifluoroethyl)imidazolidin-2-one 3 and (−)-1-[[6-(difluoromethyl)-2-(methoxymethyl)imidazo[2,1-b][1,3,4]thiadiazol-5-yl]methyl]-4-(2,2,2-trifluoroethyl)imidazolidin-2-one 4

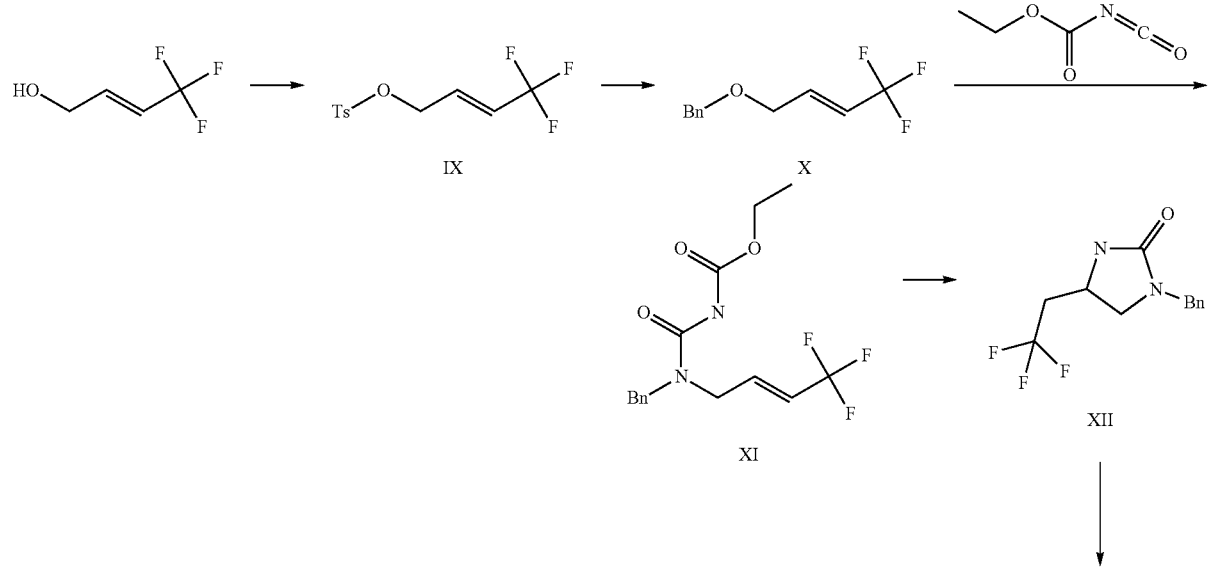

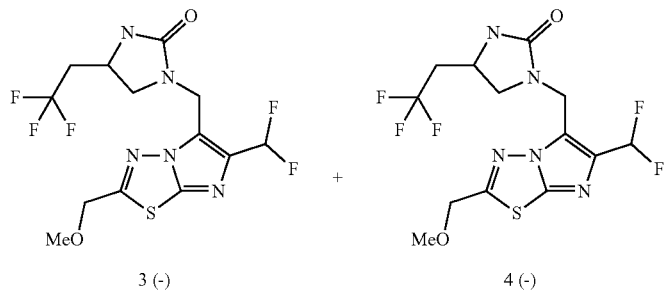
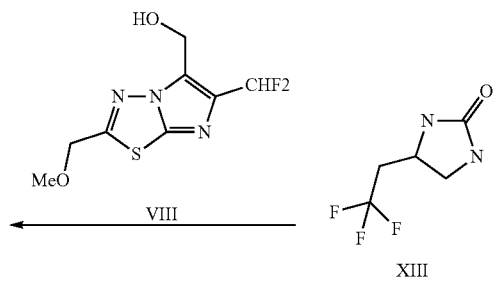

2.1 Synthesis of [(E)-4,4,4-trifluorobut-2-enyl] 4-methylbenzenesulfonate IX To a mixture of 4,4,4-trifluorobut-2-en-1-ol (1.0 eq., 15 g, 118.9 mmol) in dichloromethane (100 mL) at 0° C. was successively added triethylamine (1.0 eq., 17 mL, 120.6 mmol) and a solution of p-toluenesulfonyl chloride (1.0 eq., 22.7 g, 119 mmol) in dichloromethane (25 mL). The mixture was stirred at room temperature for 16 h (the conversion was checked by TLC). The organic layer was washed with water (three times), with brine (two times), dried over $MgSO_4$, filtered and evaporated to dryness to give a yellow oil (16 g). The crude was purified via preparative LC ($SiO_2$ 10 µm, diam 8 cm, 1.2 kg, $CH_2Cl_2$/Heptane gradient from 10/90 to 15/85) to give [(E)-4,4,4-trifluorobut-2-enyl] 4-methylbenzenesulfonate IX (8.0 g, 28.5 mmol) as a yellow oil.
Yield: 24%
LC/MS: $[M+H]^+=281.3$
$^1$H NMR (400 MHz, DMSO-$d_6$): δ 7.83 (t, J=8.4 Hz, 2H), 7.50 (dd, J=8.4, 2.1 Hz, 2H), 6.54-6.00 (m, 2H), 4.81 (dtt, J=21.3, 4.8, 2.3 Hz, 2H), 2.43 (d, J=2.1 Hz, 3H).

2.2 Synthesis of (E)-N-benzyl-4,4,4-trifluoro-but-2-en-1-amine X

To a solution of benzylamine (1.5 eq., 4.8 mL, 43 mmol) in a mixture of isopropyl acetate (3 mL) and 2-propanol (6.3 mL) were added potassium carbonate (1.0 eq., 4 g, 28.6 mmol) and potassium iodide (0.08 eq., 380 mg, 2.3 mmol). The mixture was stirred to 60° C. and water (22 mL) was added to homogenize the solution. To the reaction mixture at 60° C. was added dropwise, during 2 h, a solution of [(E)-4,4,4-trifluorobut-2-enyl] 4-methylbenzenesulfonate IX (1.0 eq., 8 g, 28.5 mmol) in isopropyl acetate (3 mL) and the mixture was stirred at 60° C. for 3 h. The crude mixture was treated with water (30 mL) and the aqueous layer was extracted with isopropyl acetate (two times). The combined organic layers were successively washed with an aqueous saturated solution of $NH_4Cl$ and brine, dried over $MgSO_4$, filtered and evaporated to dryness to give (E)-N-benzyl-4,4,4-trifluoro-but-2-en-1-amine X (5.5 g, 21 mmol) as a crude yellow oil. The crude was used directly in the next step without any further purification
Estimated Yield: 73%
LC/MS: $[M+H]^+=216.2$
NMR (400 MHz, DMSO-$d_6$): δ 7.39-7.14 (m, 5H), 6.60-5.78 (m, 2H), 3.68 (d, J=6.2 Hz, 2H), 3.42-3.18 (m, 2H).

2.3. Synthesis of ethyl N-[benzyl-[(E)-4,4,4-trifluorobut-2-enyl]carbamoyl]carbamate XI To a mixture of (E)-N-benzyl-4,4,4-trifluoro-but-2-en-1-amine X (1.0 eq., 5.5 g, 26 mmol) in 2-methyltetrahydrofuran (35 mL) at 0° C. was added, dropwise, a solution of ethoxycarbonylisocyanate (1.0 eq., 2.9 mL, 26 mmol, 90 mass %) in 2-methyltetrahydrofuran (16 mL). The mixture was stirred at 0° C. for 0.5 h, then treated with water (15 mL) and allowed to warm up to 10° C. After addition of acetic acid (3 mL) the organic layer was washed with brine, dried over $MgSO_4$, filtered and evaporated to dryness to give a beige oil (8.8 g). The crude was purified by flash chromatography Biotage Isolera Four (100 g KP-SNAP silica gel column in a gradient of 0% to 1% methanol in dichloromethane over 12 CV). The purest fractions were evaporated and dried under high vacuum to give ethyl N-[benzyl-[(E)-4,4,4-trifluorobut-2-enyl]carbamoyl]carbamate XI (3.3 g, 10 mmol) as a white solid.
Yield: 39%
LC/MS: $[M+H]^+=331.3$
$^1$H NMR (400 MHz, DMSO-$d_6$): δ 9.65 (d, J=35.1 Hz, 1H), 7.42-7.15 (m, 5H), 6.47-5.82 (m, 2H), 4.51 (d, J=8.6 Hz, 2H), 4.19-3.99 (m, 4H), 1.20 (td, J=7.2, 1.4 Hz, 3H)

2.4 Synthesis of 1-benzyl-4-(2,2,2-trifluoroethyl)imidazolidin-2-one XII

A mixture of ethyl N-[benzyl-[(E)-4,4,4-trifluorobut-2-enyl]carbamoyl]carbamate XI (1.0 eq., 69.7 g, 179 mmol, 85 mass %) and sodium hydroxide (1.0 eq., 7.32 g, 179 mmol) in 2,2,2-trifluoroethanol (250 mL) was stirred at 80° C. for 120 h (the reaction was checked by LC/MS). After evaporation of the solvent under reduce pressure, the obtained paste was taken up in dichloromethane. The organic layer was washed with water (two times), dried over $Na_2SO_4$, filtered and evaporated to dryness to give a beige paste which was triturated in diethyl ether, filtered and washed with diethyl ether to give 1-benzyl-4-(2,2,2-trifluoroethyl)imidazolidin-2-one XII (29.43 g, 114.0 mmol) as a white solid.
Estimated Yield: 63%
LC/MS: $[M+H]^+=259.2$
$^1$H NMR (400 MHz, DMSO-$d_6$): δ 7.42-7.18 (m, 5H), 6.71 (s, 1H), 4.25 (q, J=15.1 Hz, 2H), 3.93-3.73 (m, 1H), 3.41 (t, J=8.8 Hz, 1H), 2.96 (dd, J=8.9, 7.1 Hz, 1H), 2.55 (dt, J=11.9, 3.5 Hz, 1H), 2.47-2.35 (m, 1H).

2.5 Synthesis of 4-(2,2,2-trifluoroethyl)imidazolidin-2-one XIII

To a mixture of 1-benzyl-4-(2,2,2-trifluoroethyl)imidazolidin-2-one XII (1.0 eq., 5.0 g, 19.3 mmol) and potassium bromide (1.0 eq., 2.30 g, 19.3 mmol) in a blend of dichloromethane (100 mL) and water (12.5 mL), at room temperature, was added potassium peroxymonosulfate (Oxone®, 1.5 eq., 17.8 g, 29.0 mmol,). The mixture was stirred for 24 h at 30° C. An aqueous saturated solution of Na₂SO₃ was added to the mixture and the aqueous layer was extracted with ethyl acetate (three times). The combined extracts were washed with brine, dried over MgSO₄, filtered and evaporated to dryness. The obtained mixture was triturated in methanol, filtered and purified by flash chromatography Biotage Isolera Four (50 g KP-SNAP silica gel column in a gradient of 0% to 5% methanol in dichloromethane over 12 CV). The purest fraction were evaporated to dryness to give 4-(2,2,2-trifluoroethyl)imidazolidin-2-one XIII (1.8 g, 10 mmol).

Yield: 53%

LC/MS: $[M+H]^+$=169.1

¹H NMR (400 MHz, DMSO-$d_6$) δ 6.39 (s, 1H), 6.29 (s, 1H), 3.88 (ttd, J=8.5, 6.4, 1.9 Hz, 1H), 3.47 (t, J=8.7 Hz: 1H), 3.05 (t, J=8.0 Hz, 1H), 2.55 (ddd, J=15.5, 7.7, 4.4 Hz, 1H), 2.49-2.42 (m, 1H).

2.6 Synthesis of (+)-1-[[6-(difluoromethyl)-2-(methoxymethyl)imidazo[2,1-b][1,3,4]thiadiazol-5-yl]methyl]-4-(2,2,2-trifluoroethyl)imidazolidin-2-one 3 and (+1-[[6-(difluoromethyl)-2-(methoxymethyl)imidazo[2,1-b][1,3,4]thiadiazol-5-yl]methyl]-4-(2,2,2-trifluoroethyl)imidazolidin-2-one 4

To a mixture of [6-(difluoromethyl)-2-(methoxymethyl)imidazo[2,1-b][1,3,4]thiadiazol-5-yl]methanol VIII (1.0 eq., 350 mg, 1.4 mmol) and 4-(2,2,2-trifluoroethyl)imidazolidin-2-one XIII (1.5 eq., 354 mg, 2.1 mmol) in sulfolane (2 mL), was added p-toluenesulfonic acid monohydrate (1.0 eq., 267 mg, 1.4 mmol) and the mixture was stirred at 110° C. for 3 h. The mixture was cooled to room temperature and was purified by preparative reverse phase HPLC (KROMASIL-Eternity XT C18 10 μm, ACN/H₂O/NH₄OH gradient from 05/95/0.1 to 95/05/0.1) to give a white solid (260 mg: mixture of regioisomers) which was purified by achiral SFC (Phenomenex SiO₂ Beta 50×340 mm, CO₂/EtOH co-solvent gradient from 1% to 40%/150 bars/360 mL/min) to give the expected regioisomer as white solid (143 mg of racemate). The two enantiomers of the major regioisomer were separated by chiral SFC (Phase: LuxCell4, CO₂/EtOH co-solvent 20%/360 mL/min) to give (+)-1-[[6-(difluoromethyl)-2-(methoxymethyl)imidazo[2,1-b][1,3,4]thiadiazol-5-yl]methyl]-4-(2,2,2-trifluoroethyl)imidazolidin-2-one 3 (first eluted, 4.3-5.8 min., 52 mg, 0.13 mmol) and (+1-[[6-(difluoromethyl)-2-(methoxymethyl)imidazo[2,1-b][1,3,4]thiadiazol-5-yl]methyl]-4-(2,2,2-trifluoroethyl)imidazolidin-2-one 4 (second eluted, 6.5-9 min., 52 mg, 0.13 mmol) as white solids.

Yields: 9%

LC/MS: $[M+H]^+$=400.3

NMR (400 MHz, CDCl₃): δ 6.84 (t, J=54.6 Hz, 1H), 4.90-4.65 (m, 4H), 3.97 (dd, J=7.9, 5.6 Hz, 1H), 3.60 (t, J=8.8 Hz, 1H), 3.08 (dd, J=9.0, 7.0 Hz, 1H), 2.48-2.18 (m, 2H).

Alpha-D (3, MeOH, 10 mg/mL, 28.6° C.)=+13.2

Alpha-D (4, MeOH, 10 mg/mL, 28.6° C.)=−12.8

Example 3. Synthesis of (4S)-1-[[2-[dideuterio(trideuteriomethoxy)methyl]-6-(difluoromethyl)imidazo[2,1-b][1,3,4]thiadiazol-5-yl]methyl]-4-propyl-imidazolidin-2-one 5

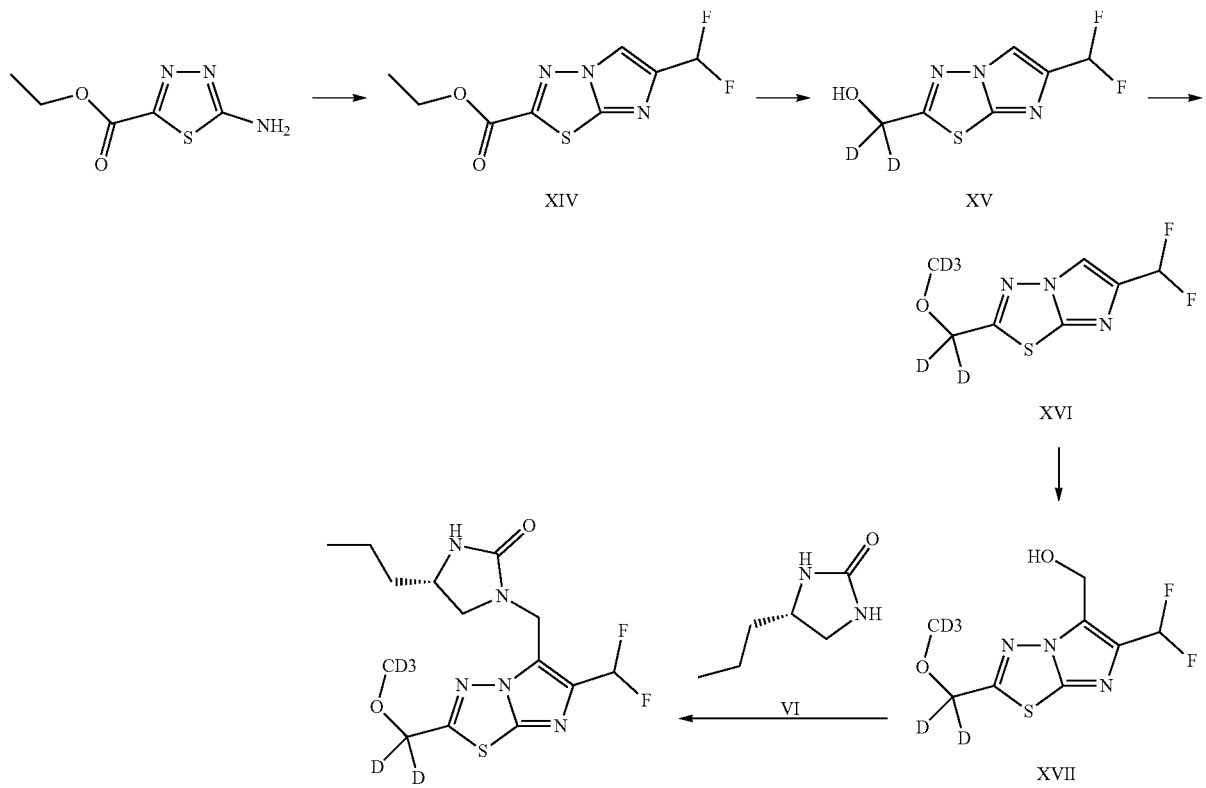

3.1 Synthesis of ethyl 6-(difluoromethyl)imidazo[2,1-b][1,3,4]thiadiazole-2-carboxylate XIV To a solution of 5-amino-1,3,4-thiadiazole-2-carboxylic acid ethyl ester (1.0 eq., 8.8 g, 50 mmol) in DMF (105 mL), at 100° C., was added (slow dropwise) a solution of 3-bromo-1,1-difluoro-propan-2-one (1.05 equiv., 9.0 g, 52 mmol) in DMF (5 mL). The reaction mixture was heated at 100° C. during 2 h. A saturated aqueous solution of NaHCO$_3$ was added and the organic layer was extracted with ethyl acetate (three times). The combined organic layers were washed with water (five times), dried over MgSO$_4$, filtered and evaporated to dryness to give a brown solid (9.0 g). The crude was purified by flash chromatography Biotage Isolera Four (100 g KP-SNAP silica gel column in a gradient of 0% to 10% methanol in dichloromethane over 14 CV) and the pure fractions were evaporated under high vacuum to give ethyl 6-(difluoromethyl)imidazo[2,1-b][1,3,4]thiadiazole-2-carboxylate XIV (4.48 g, 18.1 mmol) as a beige solid.

Yield: 36%

LC/MS: [M+H]$^+$=248.2

3.2 Synthesis of dideuterio-[6-(difluoromethyl)imidazo[2,1-b][1,3,4]thiadiazol-2-yl]methanol XV A solution of ethyl 6-(difluoromethyl)imidazo[2,1-b][1,3,4]thiadiazole-2-carboxylate XIV (1.0 eq., 4.48 g, 18.1 mmol) in ethanol (80 mL) at −20° C., was treated with sodium borodeuteride (2.0 eq., 1.52 g, 36.2 mmol). The reaction mixture was stirred at −20° C. for 20 min and was treated with a saturated solution of NH$_4$Cl. The ethanol was evaporated and the aqueous layer was extracted with dichloromethane (three times). The combined organic layers were washed with water (two times) and brine, dried over MgSO$_4$, filtered and evaporated to dryness to give dideuterio-[6-(difluoromethyl)imidazo[2,1-b][1,3,4]thiadiazol-2-yl]methanol XV (3.55 g, 17.0 mmol) as a white solid, used as such in the next step.

Yield: 93%

LC/MS: [M+H]$^+$=208.2

3.3 Synthesis of 2-[dideuterio(trideuteriomethoxy)methyl]-6-(difluoromethyl)imidazo[2,1-b][1,3,4]thiadiazole XVI To a solution of dideuterio-[6-(difluoromethyl)imidazo[2,1-b][1,3,4]thiadiazol-2-yl]methanol XV (1.0 eq., 1.77 g, 8.5 mmol) in methanol (50 mL), at room temperature, were successively added silver oxide (1.3 eq., 2.57 g, 11.1 mmol) and iodomethane-d$_3$ (4 equiv., 4.96 g, 34.2 mmol). The reaction mixture was stirred at 40° C. during 16 h, then was filtered and concentrated to dryness to give a yellow oil. The crude was purified by flash chromatography Biotage Isolera Four (100 g KP-SNAP silica gel column in a gradient of 0% to 2% methanol in dichloromethane over 12 CV) to give 2-[dideuterio(trideuteriomethoxy)methyl]-6-(difluoromethyl)imidazo[2,1-b][1,3,4]thiadiazole XVI (1.12 g, 4.84 mmol) as a white solid.

Yield: 57%

LC/MS: [M+H]$^+$=225.2

$^1$H NMR (400 MHz, DMSO-d$_6$): δ 8.53 (t, J=2.2 Hz, 1H), 7.01 (t, J=54.6 Hz, 1H).

3.4 Synthesis of [2-[dideuterio(trideuteriomethoxy)methyl]-6-(difluoromethyl)imidazo[2,1-b][1,3,4]thiadiazol-5-yl]methanol XVII In a sealed tube, 2-[dideuterio(trideuteriomethoxy)methyl]-6-(difluoromethyl)imidazo[2,1-b][1,3,4]thiadiazole XVI (1.0 eq., 1.050 g, 4.7 mmol), paraformaldehyde (6.0 equiv., 28.1 mmol) and an aqueous solution of hydrochloric acid (2N) (0.9 equiv., 2.1 mL, 4.2 mmol) were mixed in 1,4-dioxane (2 mL). The mixture was stirred at 90° C. for 2 h and the reaction was checked by LC/MS. The crude mixture was cooled to RT and an aqueous saturated solution of NaHCO$_3$ was added until pH=6-7. The aqueous layer was extracted with ethyl acetate (3 times) and the combined organic layers were washed with brine, dried over MgSO$_4$, filtered and evaporated to dryness. The crude was purified by flash chromatography Bipotage Isolera Four (25 g KP-SNAP silica gel column in a gradient of 0% to 10% methanol in dichloromethane over 12 CV) to give a yellow oil (1.03 g) which was purified a second time by preparative reverse phase HPLC (KROMASIL-Eternity XT C18 10 μm, ACN/H$_2$O/NH$_4$O H gradient from 10/90/0.1 to 40/60/0.1). The purest fractions were evaporated to dryness to give [2-[dideuterio(trideuteriomethoxy)methyl]-6-(difluoromethyl)imidazo[2,1-b][1,3,4] thiadiazol-5-yl]methanol XVII (536 mg, 2.1 mmol) as a beige solid.

Yield: 45%

LC/MS: [M+H]$^+$=255.3

$^1$H NMR (400 MHz, DMSO-d$_6$): δ 7.11 (t, J=53.6 Hz, 1H), 5.47 (t, J=5.5 Hz, 1H), 4.79 (dt, J=5.4, 1.2 Hz, 2H).

3.5 Synthesis of (4S)-1-[[2-[dideuterio(trideuteriomethoxy)methyl]-6-(difluoromethyl)imidazo[2,1-b][1,3,4]thiadiazol-5-yl]methyl]-4-propyl-imidazolidin-2-one 5

To a mixture of [2-[dideuterio(trideuteriomethoxy)methyl]-6-(difluoromethyl)imidazo[2,1-b][1,3,4]thiadiazol-5-yl]methanol XVII (1.0 eq., 100 mg, 0.39 mmol) and (4S)-4-propylimidazolidin-2-one VI (2.0 eq., 0.78 mmol) in sulfolane (2 mL), was added p-toluenesulfonic acid monohydrate (1.0 eq., 0.39 mmol) and the mixture was stirred at 110° C. for 2 h. The mixture was cooled to room temperature and was directly purified by reverse phase preparative HPLC (basic conditions) to give a beige solid (83 mg of the mixture of regioisomers) which was purified by achiral SFC (Phenomenex SiO$_2$ Beta 50×340 mm, CO$_2$/EtOH co-solvent gradient from 1% to 40%/150 bars/360 mL/min) to give the expected regioisomer as an oil (42 mg). This isolated regioisomer was purified another time by preparative HPLC (basic conditions) to give (4S)-1-[[2-[dideuterio(trideuteriomethoxy)methyl]-6-(difluoromethyl)imidazo[2,1-b][1,3,4]thiadiazol-5-yl]methyl]-4-propyl-imidazolidin-2-one 5 (27 mg, 0,074 mmol) as a white solid.

Yield: 19%

LC/MS: [M+H]$^+$=365.4

$^1$H NMR (400 MHz, DMSO-d$_6$): δ 7.12 (t, J=53.4 Hz, 1H), 6.76 (s, 1H), 4.72-4.48 (m, 2H), 3.46 (h, J=5.9 Hz, 1H), 3.36 (t, J=8.4 Hz, 1H), 2.84 (dd, J=8.4, 6.7 Hz, 1H), 1.42-1.10 (m, 4H), 0.83 (t, J=7.1 Hz, 3H).

(4R)-1-[[2-[dideuterio(trideuteriomethoxy)methyl]-6-(difluoromethyl)imidazo[2,1-b][1,3,4]thiadiazol-5-yl]methyl]-4-propyl-imidazolidin-2-one 6 is prepared according to the same procedure starting from (4R)-4-propylimidazolidin-2-one VIA. Yield: 25%

Example 4. Synthesis of (4S)-1-[[2-[dideuterio (methoxy)methyl]-6-(difluoromethyl)imidazo[2,1-b] [1,3,4]thiadiazol-5-yl]methyl]-4-propyl-imidazolidin-2-one 7

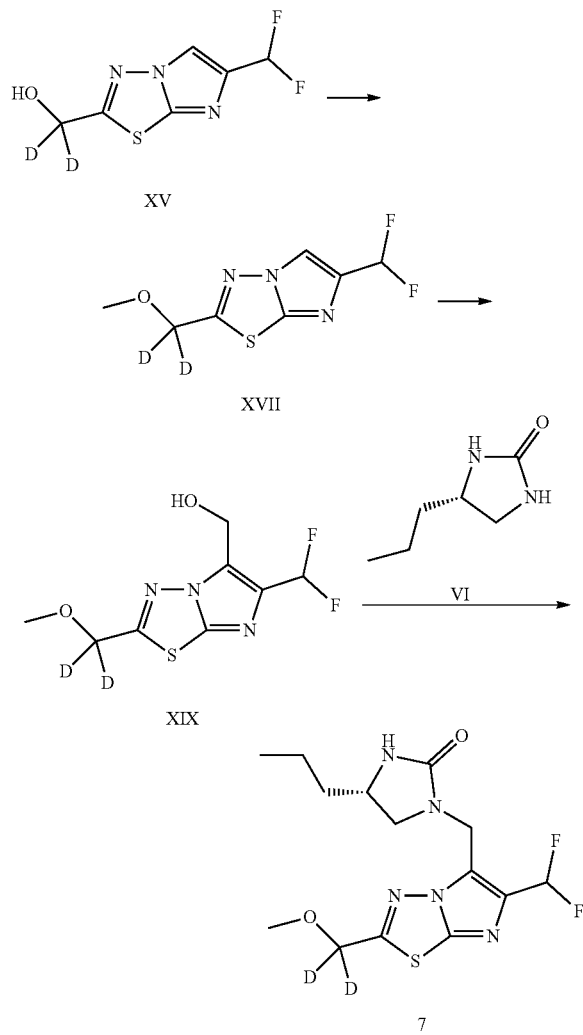

4.1 Synthesis of 2-[dideuterio(methoxy)methyl]-6-(difluoromethyl)imidazo[2,1-b][1,3,4]thiadiazole XVIII To a solution of dideuterio-[6-(difluoromethyl)imidazo[2,1-b][1,3,4]thiadiazol-2-yl]methanol XV (1.0 eq., 1.77 g, 8.5 mmol) in methanol (50 mL), at room temperature, were successively added silver oxide (1.3 eq., 2.57 g, 11.1 mmol) and iodomethane (4.0 equiv., 4.96 g, 34.0 mmol). The reaction mixture was stirred at 40° C. during 16 h, then was filtered and concentrated to dryness to give a yellow oil. A saturated aqueous solution of NaHCO$_3$ was added and the aqueous layer was extracted with ethyl acetate (three times). The combined organic layers were dried over MgSO$_4$, filtered and evaporated to dryness to give a yellow oil.

The crude was purified by flash chromatography Biotage Isolera Four (100 g KP-SNAP silica gel column in a gradient of 0% to 2% methanol in dichloromethane over 15 CV) to give 2-[dideuterio(methoxy)methyl]-6-(difluoromethyl)imidazo[2,1-b][1,3,4]thiadiazole XVIII (1.24 g, 5.43 mmol) as a yellow solid.

Yield: 63%

LC/MS: [M+H]$^+$=222.2

$^1$H NMR (400 MHz, DMSO-d$_6$): δ 8.54 (t, J=2.2 Hz, 1H), 7.01 (t, J=54.6 Hz, 1H), 3.43 (s, 3H).

4.2 Synthesis of [2-[dideuterio(methoxy)methyl]-6-(difluoromethyl)imidazo[2,1-b][1,3,4]thiadiazol-5-yl]methanol XIX In a sealed tube, 2-[dideuterio(methoxy)methyl]-6-(difluoromethyl)imidazo[2,1-b][1,3,4]thiadiazole XVIII (1.0 eq., 1.18 g, 5.33 mmol), paraformaldehyde (6.0 eq., 960 mg 32.0 mmol) and an aqueous solution of hydrochloric acid (2N) (0.9 eq., 2.4 mL, 4.80 mmol) were mixed in 1,4-dioxane (2.2 mL). The mixture was stirred at 90° C. for 2 h and the reaction was checked by LC/MS. The crude mixture was cooled to RT and an aqueous saturated solution of NaHCO$_3$ was added until pH=6-7. The aqueous layer was extracted with ethyl acetate (three times) and the combined organic layers were washed with brine, dried over MgSO$_4$, filtered and evaporated to dryness. The crude was purified by flash chromatography Bipotage Isolera Four (25 g KP-SNAP silica gel column in a gradient of 0% to 10% methanol in dichloromethane over 12 CV) to give a yellow oil (910 mg) which was purified a second time by preparative reverse phase HPLC (KROMASIL-Eternity XT C18 10 μm, ACN/H$_2$O/NH$_4$OH gradient from 10/90/0.1 to 40/60/0.1). The purest fractions were evaporated to dryness to give [2-[dideuterio(methoxy)methyl]-6-(difluoromethyl)imidazo[2,1-b][1,3,4]thiadiazol-5-yl]methanol XIX (596 mg, 2.37 mmol) as a white solid.

Yield: 44%

LC/MS: [M+H]$^+$=252.2

$^1$H NMR (400 MHz, DMSO-d6) δ 7.11 (t, J=53.5 Hz, 1H), 5.47 (t, J=5.4 Hz, 1H), 4.80 (dt, J=5.5, 1.2 Hz, 2H), 3.43 (s, 3H).

4.3 Synthesis of (4S)-1-[[2-[dideuterio(methoxy) methyl]-6-(difluoromethyl)imidazo[2,1-b][1,3,4] thiadiazol-5-yl]methyl]-4-propyl-imidazolidin-2-one 7

To a mixture of [2-[dideuterio(methoxy)methyl]-6-(difluoromethyl)imidazo[2,1-b][1,3,4]thiadiazol-5-yl]methanol XIX (1.0 eq., 100 mg, 0.39 mmol) and (4S)-4-propylimidazolidin-2-one VI (2.0 eq., 102 mg, 0.79 mmol) in sulfolane (2 mL), was added p-toluenesulfonic acid monohydrate (1.0 eq., 76 mg, 0.39 mmol) and the mixture was stirred at 110° C. for 2 h. The mixture was cooled to room temperature and was directly purified by reverse phase preparative HPLC (basic conditions) to give a beige solid (83 mg of the mixture of regioisomers) which was purified by achiral SFC (Phenomenex SiO$_2$ Beta 50×340 mm, CO$_2$/EtOH Co-solvent gradient from 1% to 40%/150 bars/360 mL/min) to give (4S)-1-[[2-[dideuterio(methoxy)methyl]-6-(difluoromethyl) imidazo[2,1-b][1,3,4]thiadiazol-5-yl]methyl]-4-propyl-imidazolidin-2-one 7 (28 mg, 0.08 mmol) as a beige solid.

Yield: 19%

LC/MS: [M+H]$^+$=362.4

$^1$H NMR (400 MHz, DMSO-d$_6$): δ 7.12 (t, J=53.4 Hz, 1H), 6.76 (s, 1H), 4.73-4.48 (m, 2H), 3.43 (s, 4H), 3.36 (t, J=8.4 Hz, 1H), 2.84 (dd, J=8.3, 6.7 Hz, 1H), 1.43-1.08 (m, 4H), 0.82 (t, J=7.0 Hz, 3H).

(4R)-1-[[2-[dideuterio(methoxy)methyl]-6-(difluoromethyl)imidazo[2,1-b][1,3,4]thiadiazol-5-yl]methyl]-4-propyl-imidazolidin-2-one 8 is prepared according to the same procedure starting from (4R)-4-propylimidazolidin-2-one VIA. Yield: 29%.

Example 5. Synthesis of (−)-4-(2-chloro-2,2-difluoro-ethyl)-1-[[6-(difluoromethyl)-2-(methoxymethyl)imidazo[2,1-b][1,3,4]thiadiazol-5-yl]methyl] imidazolidin-2-one 9 and (+)-4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one 10 gradient ACN/H$_2$O/NH$_4$OH Gr 40/70/0.1%) to give ethyl 3-benzyl-5-(2,2-difluorovinyl)-2-oxo-imidazolidine-1-carboxylate XX (7.1 g, 21.5 mmol) as a yellow oil.
Yield: 37%
LC/MS: [M+H]$^+$=311.07
$^1$H NMR (400 MHz, DMSO-d$_6$): δ 7.47-7.16 (m, 5H), 4.98-4.71 (m, 2H), 4.34 (s, 2H), 4.22-4.01 (m, 2H), 3.54 (td, J=9.1, 1.4 Hz, 1H), 3.03-2.96 (m, 1H), 1.20 (t, J=7.1 Hz, 3H).

5.2 Synthesis of 1-benzyl-4-(2-chloro-2,2-difluoro-ethyl)imidazolidin-2-one XXI

A solution of ethyl 3-benzyl-5-(2,2-difluorovinyl)-2-oxo-imidazolidine-1-carboxylate XX (1.0 eq., 6.1 g, 20 mmol) in

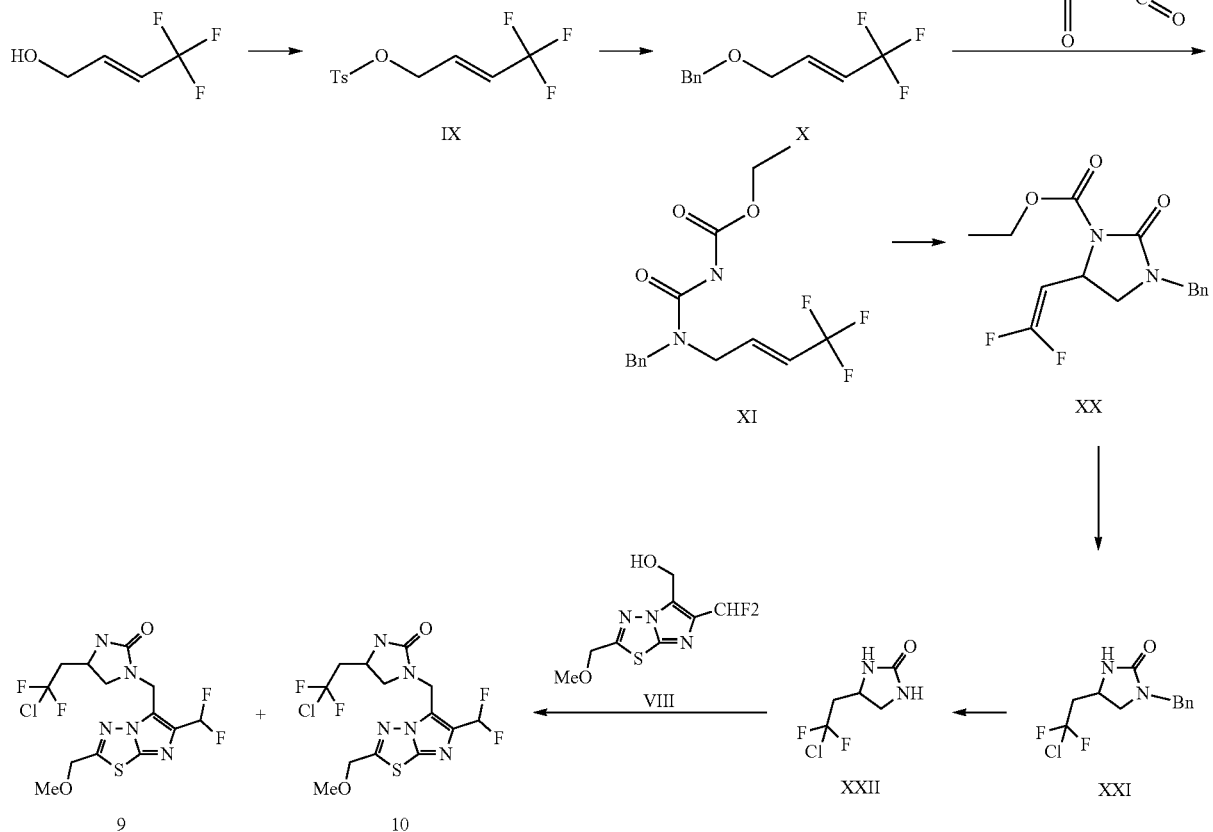

5.1 Synthesis of ethyl 3-benzyl-5-(2,2-difluorovinyl)-2-oxo-imidazolidine-1-carboxylate XX To a mixture of ethyl N-[benzyl-[(E)-4,4,4-trifluorobut-2-enyl]carbamoyl]carbamate XI (1.0 eq., 39 g, 118 mmol) in DMF (790 mL) was added potassium tert-butoxide (1.1 eq., 14.6 g, 130 mmol) and the mixture was stirred at 75° C. for 5 h. Water was then added and the aqueous layer was extracted with ethyl acetate (3 times). The combined organic layers were washed with water and brine, dried over MgSO$_4$, filtered and evaporated until dryness to give a yellow oil which was purified by preparative chromatography in normal phase (1.2 kg silica gel column in 100% dichloromethane) The obtained impure compound was purified a second time by reverse phase preparative HPLC (KROMASIL-Eternity XT C18 10 μm 8*14 cm 500 g a mixture of hydrochloric acid (0.32 M, 61 ml) and acetic acid (3.2 M, 6.1 ml) was stirred at 70° C. for 88 h. The mixture was neutralized with a saturated aqueous solution of NaHCO$_3$ until pH 6-7 and the aqueous layer was extracted with ethyl acetate (2 times), washed with brine, dried over MgSO$_4$, filtered and evaporated to dryness to give a brown oil which was purified by flash chromatography Biotage Isolera Four (100 g KP-SNAP silica gel column in a gradient of 0% to 5% methanol in dichloromethane over 15CV). The purest fractions were collected and evaporated to dryness to give 1-benzyl-4-(2-chloro-2,2-difluoro-ethyl)imidazolidin-2-one XXI (4.2 g, 13.0 mmol) as a white solid.
Yield: 65%
LC/MS: [M+H]$^+$=275.04

$^1$H NMR (400 MHz, DMSO-d$_6$): δ 7.44-7.20 (m, 6H), 6.71 (d, J=2.0 Hz, 1H), 4.37-4.15 (m, 2H), 3.90 (pd, J=6.8, 1.9 Hz, 1H), 3.44 (t, J=8.8 Hz, 1H), 3.00 (dd, J=9.0, 7.2 Hz, 1H), 2.84-2.58 (m, 2H).

5.3 Synthesis of 4-(2-chloro-2,2-difluoro-ethyl)imidazolidin-2-one XXII

To a solution of 1-benzyl-4-(2-chloro-2,2-difluoro-ethyl) imidazolidin-2-one XXI (1.0 eq., 4.2 g, 15.0 mmol) and potassium bromide (1.0 eq., 1.8 g, 15.0 mmol) in a mixture of dichloromethane (90 ml) and water (10 ml) was added potassium peroxymonosulfate (1.5 eq., 14 g, 22.7 mmol) and the mixture was stirred for 48 h at 50° C. The mixture was cooled to room temperature and an aqueous saturated solution of Na$_2$SO$_3$ was added. The aqueous layer was extracted with ethyl acetate (3 times) and the combined organic layers were washed with brine, dried over MgSO$_4$, filtered and evaporated to dryness. The crude was purified by flash chromatography Biotage Isolera Four (100 g KP-SNAP silica gel column in a gradient of 0% to 5% methanol in dichloromethane over 15CV) to give a brown solid. The brown solid was taken up in diethyl ether and the obtained solid was filtered, washed with diethyl ether and dried to give 4-(2-chloro-2,2-difluoro-ethyl)imidazolidin-2-one XXII (780 mg, 4.2 mmol) as a white solid.
Yield: 28%
LC/MS: [M+H]$^+$=185.07
$^1$H NMR (400 MHz, DMSO-d$_6$): δ 6.37 (s, 1H), 6.29 (s, 1H), 3.91 (dtdd, J=8.6, 7.0, 5.7, 1.8 Hz, 1H), 3.48 (t, J=8.7 Hz, 1H), 3.07 (dd, J=9.0, 7.2 Hz, 1H), 2.83-2.56 (m, 2H).

5.4 Synthesis of (−)-4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one 9 and (+)-4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one 10

To a mixture of [6-(difluoromethyl)-2-(methoxymethyl) imidazo[2,1-b][1,3,4]thiadiazol-5-yl]methanol VIII (1.0 eq., 100 mg, 0.40 mmol) and 4-(2-chloro-2,2-difluoro-ethyl) imidazolidin-2-one XXII (1.1 eq., 85 mg, 0.46 mmol) in sulfolane (2 ml), was added p-toluenesulfonic acid monohydrate (1.0 eq., 76 mg, 0.40 mmol) and the mixture was stirred at 110° C. for 4 h. The mixture was directly purified by reverse phase chromatography in basic mode to give a clear oil. The obtained mixture was purified by achiral SFC (Phenomenex SiO$_2$ Beta 10 μm D=5 cm L=34 cm 300 gr, cosolvant EtOH from 1% to 40%) to give a white solid which was purified by chiral SFC (LuxCell4*EtOH 50%-heptane 50%-DEA 0.1%) to give (+4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one 9 (12 mg, 0.03 mmol, 7% Yield) and (+)-4-(2-chloro-2,2-difluoro-ethyl)-1-[[6-(difluoromethyl)-2-(methoxymethyl)imidazo[2,1-b][1,3,4]thiadiazol-5-yl] methyl]imidazolidin-2-one 10 (10 mg, 0.02 mmol, 6% Yield) as white solids.
Global Yield: 13% (7%+6%)
LC/MS: [M+H]$^+$=416.02
$^1$H NMR (400 MHz, CDCl$_3$): δ 6.84 (t, J=54.5 Hz, 1H), 4.79 (d, J=31.3 Hz, 5H), 4.03 (dt, J=12.1, 6.1 Hz, 1H), 3.60 (t, J=8.8 Hz, 1H), 3.52 (s, 3H), 3.08 (dd, J=9.0, 7.2 Hz, 1H), 2.65-2.42 (m, 2H).
Alpha-D (9, MeOH, 10 mg/mL, 25° C.)=−13

Example 6. Synthesis of (+)-1-[[6-(difluoromethyl)-2-(methoxymethyl)imidazo[2,1-b][1,3,4]thiadiazol-5-yl]methyl]-4-(2,2-difluoropropyl)imidazolidin-2-one 11 and (−)-1-[[6-(difluoromethyl)-2-(methoxymethyl)imidazo[2,1-b][1,3,4]thiadiazol-5-yl]methyl]-4-(2,2-difluoropropyl)imidazolidin-2-one 12

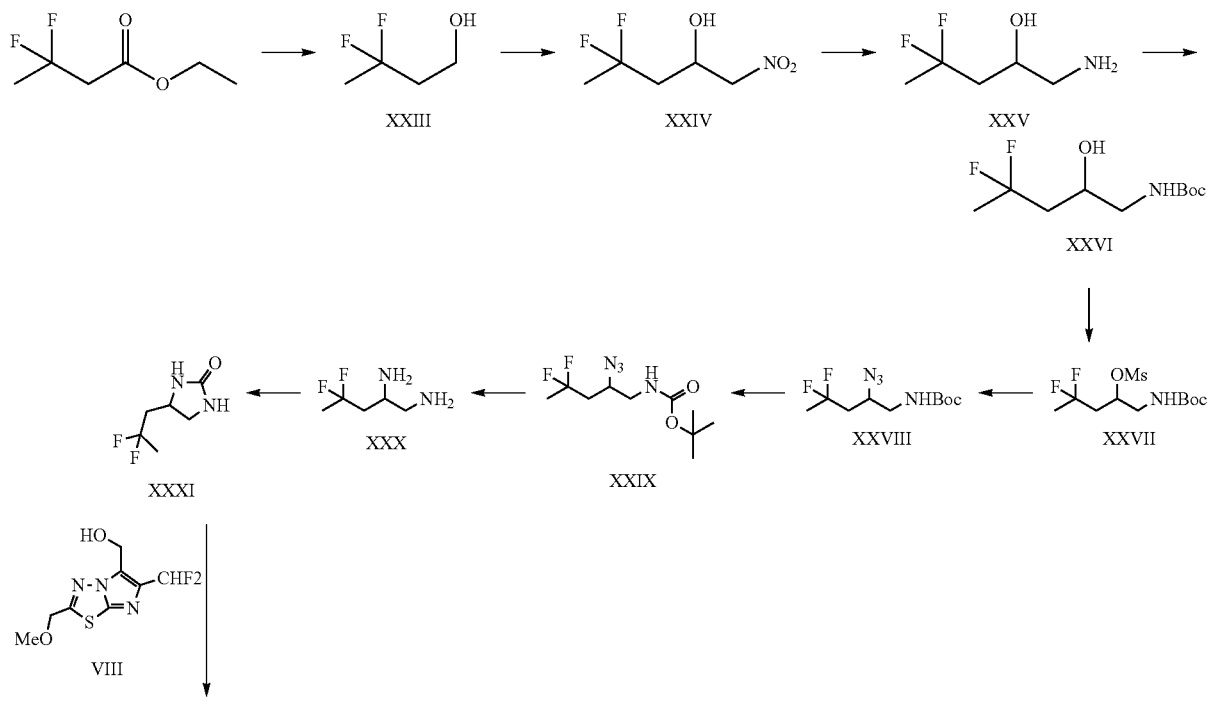

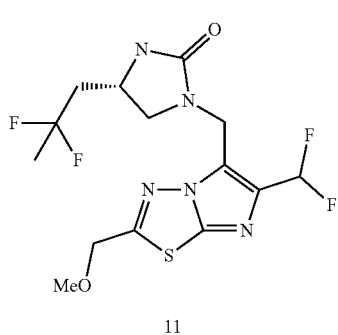 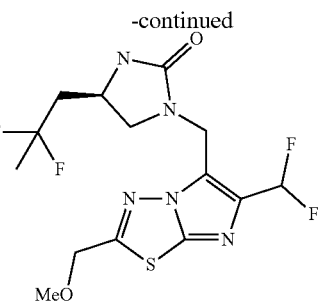

11     12

6.1 Synthesis of 3,3-difluorobutan-1-ol XXIII

To a solution of ethyl 3,3-difluorobutanoate (1.0 eq., 10 g, 65.7 mmol) in anhydrous THF (330 mL) at 0° C. was added lithium aluminium hydride (2.2 eq., 72 mL, 144.6 mmol). The reaction mixture was stirred at 0° C. during 2 h and at room temperature overnight. To the cooled solution (0° C.) was added a mixture of Glaubler's Salt ($Na_2SO_4.10H_2O$ and Celite) and water until hydrogen release was no longer evident. An additional quantity of Glaubler's reactant was added and the mixture was stirred at room temperature during 30 min. The mixture was then filtered and the filtrate was evaporated to dryness (bath temperature: max 20° C.) to give 3,3-difluorobutan-1-ol XXIII (8.8 g, 58 mmol) as pale yellow oil.

Yield: 88%

$^1$H NMR (400 MHz, DMSO-$d_6$): δ 6.95 (t, J=5.1 Hz, 1H), 5.91-5.82 (m, 4H), 4.32 (tt, J=15.9, 6.8 Hz, 2H), 4.10-4.02 (m, 2H), 3.90 (t, J=19.3 Hz, 3H).

6.2 Synthesis of 4,4-difluoro-1-nitro-pentan-2-ol XXIV

To a solution of 3,3-difluorobutan-1-ol XXIII (1.0 eq., 6.3 g, 42 mmol,) in dichloromethane (210 ml) at 0° C. was added Dess-Martin periodinane (1.2 eq., 22 g, 50 mmol) and the reaction mixture was stirred at 0° C. during 2 h. The crude mixture was then cooled at −78° C., filtered and the obtained solid washed with cold dichloromethane (−78° C.). To the filtrate warmed at room temperature was added potassium carbonate (15.0 eq., 87 g, 630 mmol) and nitromethane (30.0 eq., 77 g, 1.3 mol) and the mixture was stirred at 45° C. during 2 h. The crude mixture was filtered on Celite and the obtained filtrate was concentrated under vacuum at 30° C. to give a yellow/orange gum. The gum was purified by flash chromatography Biotage Isolera Four (100 g KP-SNAP silica gel column in 100% dichloromethane over 6 CV than 0% to 10% methanol in dichloromethane over 10 CV) to give 4,4-difluoro-1-nitro-pentan-2-ol XXIV (1.3 g, 7.5 mmol) as yellow/orange oil.

Yield: 18%

$^1$H NMR (400 MHz, CDCl$_3$): δ 4.78-4.65 (m, 1H), 4.59-4.37 (m, 2H), 2.78 (d, J=4.0 Hz, 1H), 2.33-2.02 (m, 2H), 1.71 (t, J=18.9 Hz, 3H).

6.3 Synthesis of 1-amino-4,4-difluoro-pentan-2-ol XXV

A solution of 4,4-difluoro-1-nitro-pentan-2-ol XXIV (1.0 eq., 2.0 g, 12.1 mmol) in ethanol (60 mL) was hydrogenated using a H-cube reactor equipped with a Pd/C 10% cartridge (flow 1 mL/min, 50° C., 50 bar) to give 1-amino-4,4-difluoro-pentan-2-ol XXV (1.8 g, 8.4 mmol, 69% Yield) as a colorless oil which was used in the next step without further purification.

Yield: 69%

$^1$H NMR (400 MHz, CDCl$_3$): δ 3.83 (tt, J=7.9, 3.7 Hz, 1H), 2.93-2.83 (m, 1H), 2.58 (dd, J=12.7, 8.2 Hz, 1H), 2.13-1.82 (m, 2H), 1.70 (td, J=19.0, 2.2 Hz, 3H).

6.4 Synthesis of tert-butyl N-(4,4-difluoro-2-hydroxy-pentyl)carbamate XXVI

To a solution of 1-amino-4,4-difluoro-pentan-2-ol XXV (1.0 eq., 1.8 g, 13.0 mmol) in acetonitrile (65 mL) at 0° C. was added di-tert-butyl dicarbonate (1.1 eq., 3.2 g, 14.3 mmol) and triethylamine (1.5 eq., 2.72 mL, 19.5 mmol). The mixture was stirred at 0° C. during 30 min and then at room temperature during 3 days. Water was added and the aqueous layer was extracted with dichloromethane (3 times). The combined organic layers were washed with brine, dried over MgSO$_4$, filtered and evaporated to dryness to give tert-butyl N-(4,4-difluoro-2-hydroxy-pentyl)carbamate XXVI (3.38 g, 11.3 mmol) as a yellow oil which was used in the next step without further purification.

Yield: 87%

$^1$H NMR (400 MHz, CDCl$_3$): δ 4.94 (s, 1H), 4.17-4.03 (m, 1H), 3.34 (ddd, J=14.2, 7.0, 3.3 Hz, 1H), 3.13 (dt, J=13.6, 6.3 Hz, 1H), 2.93 (s, 1H), 2.56 (q, J=7.1 Hz, 1H), 2.09-1.99 (m, 2H), 1.70 (d, J=18.9 Hz, 3H), 1.46 (d, J=10.9 Hz, 9H).

6.5 Synthesis of [1-[(tert-butoxycarbonylamino)methyl]-3,3-difluoro-butyl] Methanesulfonate XXVII To a mixture of tert-butyl N-(4,4-difluoro-2-hydroxy-pentyl)carbamate XXVI (1.0 eq., 2.5 g, 8.4 mmol) in dichloromethane (17 mL) at 0° C. was added triethylamine (3.0 eq., 3.5 mL, 25 mmol) and methanesulfonyl chloride (1.5 eq., 1 mL, 13 mmol). The mixture was stirred at 0° C. for 3 h. Water was added and the aqueous layer was extracted with dichloromethane (3 times). The combined organic layers were dried over MgSO$_4$, filtered and evaporated to dryness to give [1-[(tert-butoxycarbonylamino)methyl]-3,3-difluoro-butyl] methanesulfonate XXVII (3.09 g, 8.2 mmol) as an orange oil. The product was used without any further purification.

Yield: 99%

$^1$H NMR (400 MHz, CDCl$_3$): δ 5.15-4.89 (m, 2H), 3.66-3.50 (m, 1H), 3.46-3.30 (m, 1H), 3.05 (s, 3H), 2.50-2.09 (m, 2H), 1.69 (t, J=18.7 Hz, 3H), 1.53-1.42 (m, 9H).

6.6 Synthesis of tert-butyl N-(2-azido-4,4-difluoro-pentyl)carbamate XXVIII

To a solution of [1-[(tert-butoxycarbonylamino)methyl]-3,3-difluoro-butyl] methanesulfonate XXVII (1.0 eq., 3.1 g, 8.3 mmol) in DMF (41 mL), at room temperature, was added sodium azide (1.1 eq., 592 mg, 9.1 mmol) and the mixture was stirred at 80° C. for 12 h. The crude mixture was cooled to room temperature and water was added. The aqueous layer was extracted with ethyl acetate (3 times) and the combined organic layers were washed with water (4 times), dried over MgSO$_4$, filtered and evaporated to dryness to give an orange oil. The crude mixture was purified by flash chromatography Biotage Isolera Four (100 g KP-SNAP silica gel column in a gradient of 0% to 12% methanol in dichloromethane over 10 CV, than 12% of methanol over 4CV) to obtain tert-butyl N-(2-azido-4,4-difluoro-pentyl) carbamate XXVIII (1.2 g, 4.5 mmol) as a yellow oil.

Yield: 55%

$^1$H NMR (400 MHz, CDCl$_3$): δ 4.84 (s, 1H), 3.82 (dq, J=8.0, 5.0, 4.0 Hz, 1H), 3.41 (dt, J=11.7, 5.9 Hz, 1H), 3.10 (ddd, J=14.0, 7.7, 6.0 Hz, 1H), 2.13-1.97 (m, 2H), 1.68 (t, J=18.6 Hz, 3H), 1.47 (d, J=8.8 Hz, 9H).

6.7 Synthesis of tert-butyl N-(2-amino-4,4-difluoro-pentyl)carbamate XXIX

A solution of tert-butyl N-(2-azido-4,4-difluoro-pentyl) carbamate XXVIII (1.0 eq., 800 mg, 3.0 mmol) in ethanol (15 mL) was hydrogenated using a H-cube reactor equipped with a Pd/C 10% cartridge (flow 1 mL/min, 50° C., 50 bar) to give tert-butyl N-(2-amino-4,4-difluoro-pentyl)carbamate XXIX (718 mg, 2.86 mmol) as a colorless oil which was used in the next step without further purification.

Yield: 94%

$^1$H NMR (400 MHz, CDCl$_3$): δ 4.95 (s, 1H), 3.24 (tt, J=18.8, 4.5 Hz, 2H), 2.99 (dt, J=13.4, 6.5 Hz, 1H), 2.09-1.75 (m, 2H), 1.64 (td, J=18.7, 1.7 Hz, 3H), 1.45 (s, 9H).

6.8 Synthesis of 4,4-difluoropentane-1,2-diamine XXX

To a solution of tert-butyl N-(2-amino-4,4-difluoro-pentyl)carbamate XXIX (1.0 eq., 512 mg, 2.1 mmol) in dichloromethane (5 mL) was added trifluoroacetic acid (0.4 M, 5 mL) and the reaction mixture was stirred at room temperature during 12 h. The crude mixture was evaporated to dryness to give a beige glue which was diluted in methanol, passed through a column of StratoSpheres (SPE PL-HCO$_3$ MP SPE) and evaporated to dryness to obtained 4,4-difluoropentane-1,2-diamine XXX (330 mg, 2.3 mmol) as a beige solid (unstable product/must be directly used in the next step).

Yield: 95%

$^1$H NMR (400 MHz, CDCl$_3$): δ 3.21 (tt, J=8.1, 4.2 Hz, 1H), 2.87 (dd, J=12.7, 4.2 Hz, 1H), 2.69-2.63 (m, 2H), 2.12-1.82 (m, 1H), 1.64 (t, J=18.6 Hz, 3H).

6.9 Synthesis of 4-(2,2-difluoropropyl)imidazolidin-2-one XXXI

To a solution of 4,4-difluoropentane-1,2-diamine) XXX (1.0 eq., 330 mg, 2.4 mmol) in THF (8 mL) at room temperature was added 1,1'-carbonyldiimidazole (1.0 eq., 395 mg, 2.4 mmol) and sodium hydride (0.1 eq., 9.5 mg, 0.24 mmol). The reaction was stirred at room temperature during 16 h. A few drops of water were added (NaH neutralization) and the mixture was evaporated to dryness to give a brown solid. The crude was purified by flash chromatography Biotage Isolera Four (100 g KP-SNAP silica gel column in a gradient of 0% to 10% methanol in dichloromethane over 10 CV, than 10% of methanol over 4 CV) to give 4-(2,2-difluoropropyl)imidazolidin-2-one XXXI (156 mg, 0.95 mmol) as a beige solid.

Yield: 40%

NMR (400 MHz, CDCl$_3$): δ 4.72 (s, 1H), 4.37 (s, 1H), 4.17 (qd, J=7.8, 3.9 Hz, 1H), 3.68 (t, J=8.5 Hz, 1H), 3.32-3.04 (m, 1H), 2.39-1.98 (m, 2H), 1.66 (t, J=18.6 Hz, 3H).

6.10 Synthesis of (+)-1-[[6-(difluoromethyl)-2-(methoxymethyl)imidazo[2,1-b][1,3,4]thiadiazol-5-yl]methyl]-4-(2,2-difluoropropyl)imidazolidin-2-one 11 and (−)-1-[[6-(difluoromethyl)-2-(methoxymethyl)imidazo[2,1-b][1,3,4]thiadiazol-5-yl]methyl]-4-(2,2-difluoropropyl)imidazolidin-2-one 12

To a mixture of [6-(difluoromethyl)-2-(methoxymethyl) imidazo[2,1-b][1,3,4]thiadiazol-5-yl]methanol VIII (1.0 eq., 130 mg, 0.52 mmol) and 4-(2,2-difluoropropyl)imidazolidin-2-one XXXI (1.2 eq., 102 mg, 0.62 mmol) in sulfolane (0.2 M, 3 mL) was added p-toluenesulfonic acid monohydrate (1.0 eq., 99 mg, 0.52 mmol) and the mixture was stirred at 100° C. for 3 h. The crude was directly purified via reverse LC in basic mode to give a brown solid which was purified via achiral SFC (Phenomenex SiO$_2$ Beta 10 μm D=5 cm L=34 cm 300 gr, cosolvant EtOH 5%). The purest fractions of the major compound were evaporated to dryness to give a white solid which was purified by chiral SFC (CCO-F4*EtOH 50%-heptane 50%-DEA 0.1%) to give (+)- 1-[[6-(difluoromethyl)-2-(methoxymethyl)imidazo[2,1-b] [1,3,4]thiadiazol-5-yl]methyl]-4-(2,2-difluoropropyl)imidazolidin-2-one 11 (22 mg, 0.05 mmol) and (+1-[[6-(difluoromethyl)-2-(methoxymethyl)imidazo[2,1-b][1,3,4] thiadiazol-5-yl]methyl]-4-(2,2-difluoropropyl)imidazolidin-2-one 12 (22.5 mg, 0.06 mmol) as white solids.

Global yield: 22% (11%+11%)

LC/MS: [M+H]$^+$=396.05

$^1$H NMR (400 MHz, DMSO-d6): δ 7.13 (t, J=53.4 Hz, 1H), 6.65 (s, 1H), 4.82 (s, 2H), 4.73-4.47 (m, 2H), 3.74 (t, J=7.2 Hz, 1H), 3.43 (s, 4H), 2.99 (t, J=8.1 Hz, 1H), 2.07 (td, J=17.5, 17.0, 6.4 Hz, 2H), 1.59 (t, J=19.3 Hz, 3H).

Alpha-D (12, MeOH, 10 mg/mL, 25° C.)=−1.5

Example 7. I) Synthesis of (+)-5,5-dideuterio-1-[[6-(difluoromethyl)-2-(methoxymethyl)imidazo[2,1-b] [1,3,4]thiadiazol-5-yl]methyl]-4-propyl-imidazolidin-2-one 13 and (−)-5,5-dideuterio-1-[[6-(difluoromethyl)-2-(methoxymethyl)imidazo[2,1-b] [1,3,4]thiadiazol-5-yl]methyl]-4-propyl-imidazolidin-2-one 14

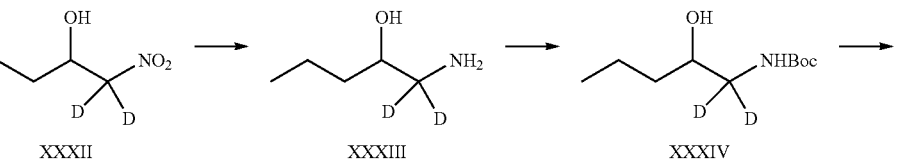

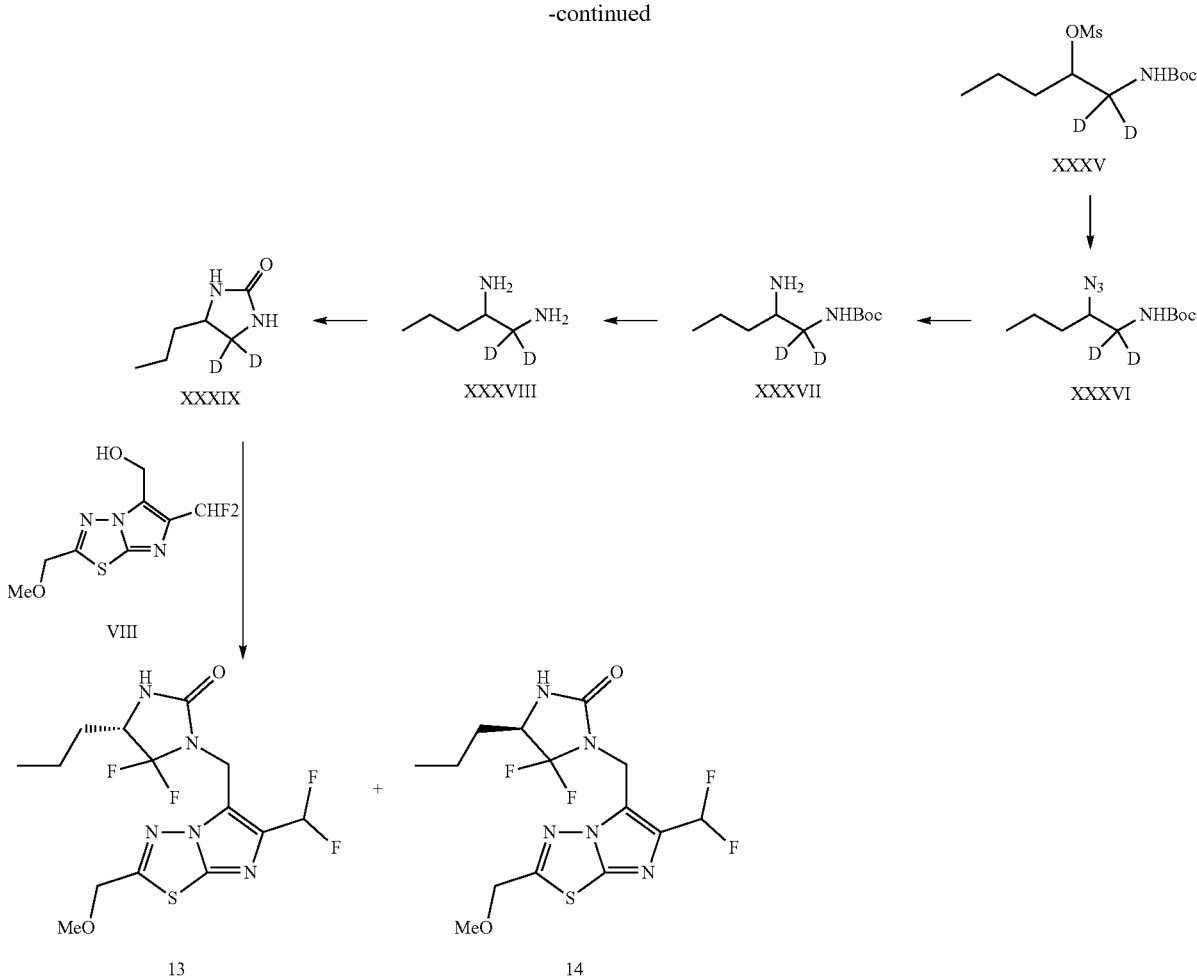

7.1 Synthesis of 1,1-dideuterio-1-nitro-pentan-2-ol XXXII

To solution of nitromethane-d3 (1.03 eq., 1.81 g, 27.9 mmol) and butyraldehyde (1.0 eq., 2.0 g, 27.2 mmol) in ethanol-d6 (7 mL) at 0° C. was added sodium deuteroxide (1.0 eq., 2.78 g, 27.2 mmol, 40 mass %) and the reaction mixture was stirred at room temperature during 16 h. Acetic acid-d4 (1.03 eq., 1793.9 mg, 27.9 mmol) was added and the reaction mixture was stirred at room temperature during 20 min. Water was then added and the aqueous layer was extracted with diethyl ether (3 times). The combined organic layers were washed with water (4 times), concentrated to dryness, dried on $Na_2SO_4$, filtered and evaporated to dryness to give an orange oil which was purified by flash chromatography Biotage Isolera Four (100 g KP-SNAP silica gel column in a gradient of 1% to 5% methanol in dichloromethane over 10 CV) to give 1,1-dideuterio-1-nitro-pentan-2-ol XXXII (2.15 g, 15.1 mmol, 95 mass %) as a yellow oil and was used as such in the next step without any further purification.

Yield: 55%

$^1$H NMR (400 MHz, $CDCl_3$): δ 4.33 (dtt, J=6.4, 4.9, 3.5, 1.6 Hz, 1H), 2.47 (d, J=5.0 Hz, 1H), 1.68-1.34 (m, 4H), 0.97 (t, J=6.9 Hz, 3H).

7.2 Synthesis of Give 1-amino-1,1-dideuterio-pentan-2-ol XXXIII

A solution of 1,1-dideuterio-1-nitro-pentan-2-ol XXXII (1.0 eq., 2.15 g, 15.9 mmol) in ethanol (80 mL) was hydrogenated using a H-cube reactor equipped with a Pd/C 10% cartridge (flow 1 mL/min, 50° C., 50 bar) to give 1-amino-1,1-dideuterio-pentan-2-ol XXXIII (1.66 g, 14.2 mmol, 90 mass %) as a colorless oil which was used as such in the next step without any further purification.

Yield: 89%

$^1$H NMR (400 MHz, $CDCl_3$): δ 3.50 (dd, J=7.4, 3.9 Hz, 1H), 1.58-1.31 (m, 4H), 0.93 (dd, J=7.6, 6.2 Hz, 3H).

7.3 Synthesis of tert-butyl N-(1,1-dideuterio-2-hydroxy-pentyl)carbamate XXXIV To a solution of 1-amino-1,1-dideuterio-pentan-2-ol XXXIII (1.0 eq., 1.86 g, 15.9 mmol, 90 mass %) in dichloromethane (80 mL), at 0° C., was added di-tert-butyl dicarbonate (1.1 eq., 3.90 g, 17.5 mmol) and triethylamine (1.5 eq., 2.42 g, 23.9 mmol). The mixture was stirred at 0° C. during 30 min and then at RT during 3 days. Water was added and the aqueous layer was extracted with dichloromethane (3 times). The combined organic layers were washed with brine, dried over $MgSO_4$, filtered and evaporated to dryness to give tert-butyl N-(1,1-dideuterio-2-hydroxy-pentyl)carbamate XXXIV (3.38 g, 15.6 mmol) as a yellow oil which was used as such in the next step without any further purification.

Yield: 98%

$^1$H NMR (400 MHz, CDCl$_3$): δ 4.88 (s, 1H), 3.70 (d, J=5.7 Hz, 1H), 2.20 (s, 1H), 1.52-1.35 (m, 13H), 0.97-0.84 (m, 3H).

7.4 Synthesis of 1-[(tert-butoxycarbonylamino)-dideuterio-methyl]butyl Methanesulfonate XXXV To a solution of tert-butyl N-(1,1-dideuterio-2-hydroxy-pentyl)carbamate XXXIV (1.0 eq., 3.6 g, 18 mmol) in dichloromethane (35 mL), at 0° C., was added triethylamine (3.0 eq., 5.4 g, 53 mmol) and methanesulfonyl chloride (1.5 eq., 3.0 g, 26 mmol). The mixture was stirred at 0° C. for 3 h, then water was added and the aqueous layer was extracted with dichloromethane (3 times). The combined organic layers were dried over MgSO$_4$, filtered and evaporated to dryness to give an orange oil which was purified by flash chromatography (100 g KP-SNAP silica gel column in a gradient of 0% to 10% methanol in dichloromethane over 10CV, then 10% of methanol over 4CV) to give 1-[(tert-butoxycarbonylamino)-dideuterio-methyl]butyl methanesulfonate XXXV (3.09 g, 9.27 mmol, 85 mass %) was obtained as a yellow oil.

Yield: 53%

$^1$H NMR (400 MHz, CDCl$_3$): δ 4.92 (s, 1H), 4.74 (dd, J=7.3, 5.2 Hz, 1H), 3.04 (s, 3H), 1.80-1.58 (m, 2H), 1.44 (s, 11H), 0.96 (t, J=7.3 Hz, 3H).

7.5 Synthesis of tert-butyl N-(2-azido-1,1-dideuterio-pentyl)carbamate XXXVI To a solution of 1-[(tert-butoxycarbonylamino)-dideuterio-methyl]butyl methanesulfonate XXXV (1.0 eq., 3.46 g, 12.2 mmol) in DMF (60 mL), at room temperature, was added sodium azide (1.1 eq., 873 mg, 13.4 mmol) and the mixture was stirred at 80° C. for 16 h. The crude mixture was cooled to room temperature, water was added and the aqueous layer was extracted with ethyl acetate (3 times). The combined organic layers were washed with water (4 times), dried over MgSO$_4$, filtered and evaporated to dryness to give an orange oil. The crude was purified by flash chromatography (100 g KP-SNAP silica gel column in a gradient of 0% to 12% methanol in dichloromethane over 10CV, then 12% of methanol over 4CV) to give tert-butyl N-(2-azido-1,1-dideuterio-pentyl)carbamate XXXVI (1.89 g, 8.23 mmol) as a yellow oil.

Yield: 67%

$^1$H NMR (400 MHz, CDCl$_3$): δ 4.80 (s, 1H), 3.49 (s, 1H), 1.51-1.35 (m, 13H), 1.02-0.82 (m, 3H).

7.6 Synthesis of tert-butyl N-(2-amino-1,1-dideuterio-pentyl)carbamate XXXVII A solution of tert-butyl N-(2-azido-1,1-dideuterio-pentyl) carbamate XXXVI (1.0 eq., 1.9 g, 8.3 mmol) in ethanol (40 mL)) was hydrogenated using a H-cube reactor equipped with a Pd/C 10% cartridge (flow 1 mL/min, 50° C., 50 bar) to give tert-butyl N-(2-amino-1,1-dideuterio-pentyl)carbamate XXXVII (1.59 g, 7.63 mmol) as a colorless oil which was used as such in the next step without any purification.

Yield: 92%

$^1$H NMR (400 MHz, CDCl$_3$): δ 4.90 (s, 1H), 2.81 (dd, J=7.9, 4.1 Hz, 1H), 1.51-1.20 (m, 13H), 0.92 (t, J=6.9 Hz, 3H).

7.7 Synthesis of 1,1-dideuteriopentane-1,2-diamine XXXVIII

To a solution of tert-butyl N-(2-amino-1,1-dideuterio-pentyl)carbamate XXXVII (1.0 eq., 199 mg, 0.925 mmol) in dichloromethane (0.4 M, 2.4 mL) was added trifluoroacetic acid (0.4 M, 2.4 mL) and the reaction mixture was stirred at room temperature during 12 h. The crude mixture was evaporated to dryness to give a beige glue which was diluted in MeOH, passed through a column of StratoSpheres (SPE PL-HCO$_3$ MP SPE) and evaporated to dryness to obtain 1,1-dideuteriopentane-1,2-diamine XXXVIII (190 mg, 0.912 mmol) as beige oil which was used as such in the next step without any further purification (unstable product/must be directly used in the next step).

Yield: 98%

$^1$H NMR (400 MHz, CDCl$_3$): δ 2.96 (q, J=5.5, 4.7 Hz, 1H), 1.49-1.24 (m, 4H), 0.91 (t, J=7.0 Hz, 3H)

7.8 Synthesis of 4,4-dideuterio-5-propyl-imidazolidin-2-one XXXIX

To a solution of 1,1-dideuteriopentane-1,2-diamine XXXVIII (1.0 eq., 190 mg, 0.91 mmol, 50 mass %) in THF (3 mL), at room temperature, were added 1,1'-carbonyldiimidazole (1.0 eq., 151 mg, 0.91 mmol) and sodium hydride (0.1 eq., 3.6 mg, 0.09 mmol, 60 mass %). The reaction was stirred at room temperature during 4 h, then a few drops of water were added (NaH neutralization) and the mixture was evaporated to dryness to give a brown solid. The crude was purified by flash chromatography (4 g KP-SNAP silica gel column in a gradient of 0% to 10% methanol in dichloromethane over 10CV then 10% of methanol over 4CV) to give 4,4-dideuterio-5-propyl-imidazolidin-2-one XXXIX (82 mg, 0.57 mmol, 90 mass %) as a beige solid.

Yield: 62%

$^1$H NMR (400 MHz, CDCl$_3$): δ 4.50 (s, 1H), 4.29 (s, 1H), 3.78 (t, J=6.5 Hz, 1H), 1.64-1.43 (m, 2H), 1.42-1.27 (m, 2H), 0.95 (t, J=7.3 Hz, 3H).

7.9 Synthesis of (+)-5,5-dideuterio-[[6-(difluoromethyl)-2-(methoxymethyl)imidazo[2,1-b][1,3,4]thiadiazol-5-yl]methyl]-4-propyl-imidazolidin-2-one 13 and (+5,5-dideuterio-[[6-(difluoromethyl)-2-(methoxymethyl)imidazo[2,1-b][1,3,4]thiadiazol-5-yl]methyl]-4-propyl-imidazolidin-2-one 14

To a mixture of [6-(difluoromethyl)-2-(methoxymethyl) imidazo[2,1-b][1,3,4]thiadiazol-5-yl]methanol VIII (1.0 eq., 100 mg, 0.40 mmol) and 4,4-dideuterio-5-propyl-imidazolidin-2-one XXXIX (1.2 eq., 63 mg, 0.48 mmol) in sulfolane (2 mL) was added p-toluenesulfonic acid monohydrate (1.0 eq., 76 mg, 0.40 mmol) and the mixture was stirred at 100° C. for 3 h. The crude was purified by reverse phase chromatography in basic mode to give a mixture of enantiomers which were separated by chiral SFC (AS*EtOH 50%-heptane 50%-DEA 0.1%). The purest fractions were evaporated to dryness to give (+)-5,5-dideuterio-1-[[6-(difluoromethyl)-2-(methoxymethyl)imidazo[2,1-b][1,3,4]thiadiazol- 5-yl]methyl]-4-propyl-imidazolidin-2-one 13 (10.8 mg, 0.03 mmol) and (+5,5-dideuterio-1-[[6-(difluoromethyl)-2-(methoxymethyl)imidazo[2,1-b][1,3,4]thiadiazol-5-yl]methyl]-4-propyl-imidazolidin-2-one 14 (15.1 mg, 0.04 mmol) as white solids.

Global yield: 18% (7.4%+10.4%)

LC/MS: [M+H]$^+$=362.1

$^1$H NMR (400 MHz, DMSO-d6): δ 7.12 (t, J=53.4 Hz, 1H), 6.76 (s, 1H), 4.83 (s, 2H), 4.75-4.40 (m, 2H), 3.43 (s, 4H), 1.48-1.10 (m, 4H), 0.82 (t, J=7.1 Hz, 3H)

Alpha-D (14, MeOH, 10 mg/mL, 25° C.)=+5.4

Table (I) indicates the IUPAC name (or the name generated from Accelerys Draw 4.0) of the compound, the ion peak observed in mass spectroscopy and the $^1$H NMR description.

TABLE 1

Physical Characterization of Example Compounds.

| no | Compound NAME | Structure | MH$^+$ | $^1$H NMR δ (DMSO-d$_6$) |
|---|---|---|---|---|
| 1 | (4S)-1-[[6-(difluoromethyl)-2-(methoxymethyl)imidazo[2,1-b][1,3,4]thiadiazol-5-yl]methyl]-4-propyl-imidazolidin-2-one | (structure) | 360.4 | 6.85 (t, J = 54.5 Hz, 1H), 4.89-4.63 (m, 4H), 4.53 (s, 1H), 3.60 (dtd, J = 8.2, 6.6, 1.4 Hz, 1H), 3.48 (d, J = 22.2 Hz, 4H), 2.96 (dd, J = 8.6, 6.8 Hz, 1H), 1.56-1.37 (m, 2H), 1.29 (ddt, J = 13.9, 6.9, 5.2 Hz, 2H), 0.91 (t, J = 7.3 Hz, 3H). |
| 2 | (4R)-1-[[6-(difluoromethyl)-2-(methoxymethyl)imidazo[2,1-b][1,3,4]thiadiazol-5-yl]methyl]-4-propyl-imidazolidin-2-one | (structure) | 360.4 | 6.85 (t, J = 54.5 Hz, 1H), 4.89-4.63 (m, 4H), 4.53 (s, 1H), 3.60 (dtd, J = 8.2, 6.6, 1.4 Hz, 1H), 3.48 (d, J = 22.2 Hz, 4H), 2.96 (dd, J = 8.6, 6.8 Hz, 1H), 1.56-1.37 (m, 2H), 1.29 (ddt, J = 13.9, 6.9, 5.2 Hz, 2H), 0.91 (t, J = 7.3 Hz, 3H). |
| 3 | (+)-1-[[6-(difluoromethyl)-2-(methoxymethyl)imidazo[2,1-b][1,3,4]thiadiazol-5-yl]methyl]-4-(2,2,2-trifluoroethyl)imidazolidin-2-one | (structure) | 400.3 | 6.84 (t, J = 54.6 Hz, 1H), 4.90-4.65 (m, 4H), 3.97 (dd, J = 7.9, 5.6 Hz, 1H), 3.60 (t, J = 8.8 Hz, 1H), 3.08 (dd, J = 9.0, 7.0 Hz, 1H), 2.48-2.18 (m, 2H). |
| 4 | (−)-1-[[6-(difluoromethyl)-2-(methoxymethyl)imidazo[2,1-b][1,3,4]thiadiazol-5-yl]methyl]-4-(2,2,2-trifluoroethyl)imidazolidin-2-one | (structure) | 400.3 | 6.84 (t, J = 54.6 Hz, 1H), 4.90-4.65 (m, 4H), 3.97 (dd, J = 7.9, 5.6 Hz, 1H), 3.60 (t, J = 8.8 Hz, 1H), 3.08 (dd, J = 9.0, 7.0 Hz, 1H), 2.48-2.18 (m, 2H). |

TABLE 1-continued

Physical Characterization of Example Compounds.

| no | Compound NAME | Structure | MH+ | ¹H NMR δ (DMSO-d$_6$) |
|---|---|---|---|---|
| 5 | (4S)-1-[[2-[dideuterio(trideuteriomethoxy)methyl]-6-(difuloromethyl)imidazo[2,1-b][1,3,4]thiadiazol-5-yl]methyl]-4-propyl-imidazolidin-2-one | 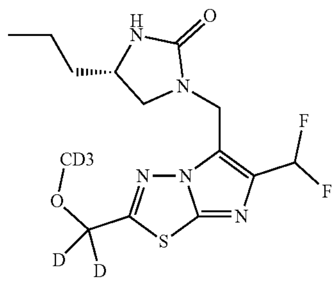 [SMILES: [2H]C([2H])([2H])OC([2H])([2H])c1nn2c(CN3C[C@H](CCC)NC3=O)c(C(F)F)nc2s1] | 365.4 | 7.12 (t, J = 53.4 Hz, 1H), 6.76 (s, 1H), 4.72-4.48 (m, 2H), 3.46 (h, J = 5.9 Hz, 1H), 3.36 (t, J = 8.4 Hz, 1H), 2.84 (dd, J = 8.4, 6.7 Hz, 1H), 1.42-1.10 (m, 4 H), 0.83 (t, J = 7.1 Hz, 3H). |
| 6 | (4R)-1-[[2-[dideuterio(trideuteriomethoxy)methyl]-6-(difluoromethyl)imidazo[2,1-b][1,3,4]thiadiazol-5-yl]methyl]-4-propyl-imidazolidin-2-one | 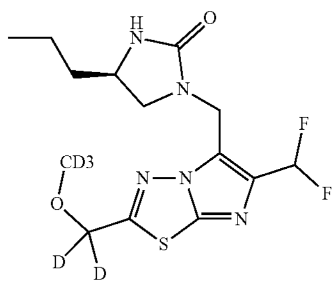 [SMILES: [2H]C([2H])([2H])OC([2H])([2H])c1nn2c(CN3C[C@@H](CCC)NC3=O)c(C(F)F)nc2s1] | 365.4 | 7.12 (t, J = 53.4 Hz, 1H), 6.76 (s, 1H), 4.72-4.48 (m, 2H), 3.46 (h, J = 5.9 Hz, 1H), 3.36 (t, J = 8.4 Hz, 1H), 2.84 (dd, J = 8.4, 6.7 Hz, 1H), 1.42-1.10 (m, 4 H), 0.83 (t, J = 7.1 Hz, 3H). |
| 7 | (4S)-1-[[2-[dideuterio(methoxy)methyl]-6-(difluoromethyl)imidazo[2,1-b][1,3,4]thiadiazol-5-yl]methyl]-4-propyl-imidazolidin-2-one | 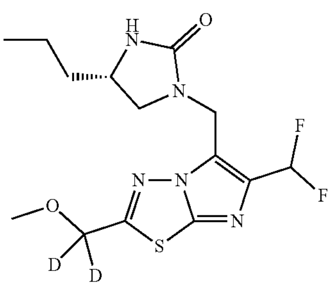 [SMILES: [2H]C([2H])(OC)c1nn2c(CN3C[C@H](CCC)NC3=O)c(C(F)F)nc2s1] | 362.4 | 7.12 (t, J = 53.4 Hz, 1H), 6.76 (s, 1H), 4.73-4.48 (m, 2H), 3.43 (s, 4H), 3.36 (t, J = 8.4 Hz, 1H), 2.84 (dd, J = 8.3, 6.7 Hz, 1H), 1.43-1.08 (m, 4H), 0.82 (t, J = 7.0 Hz, 3H). |
| 8 | (4R)-1-[[2-[dideuterio(methoxy)methyl]-6-(difluoromethyl)imidazo[2,1-b][1,3,4]thiadiazol-5-yl]methyl]-4-propyl-imidazolidin-2-one | 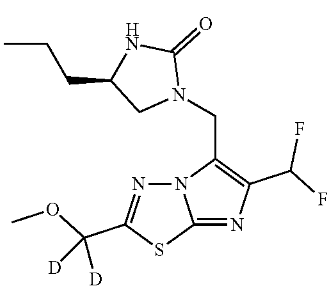 [SMILES: [2H]C([2H])(OC)c1nn2c(CN3C[C@@H](CCC)NC3=O)c(C(F)F)nc2s1] | 362.4 | 7.12 (t, J = 53.4 Hz, 1H), 6.76 (s, 1H), 4.73-4.48 (m, 2H), 3.43 (s, 4H), 3.36 (t, J = 8.4 Hz, 1H), 2.84 (dd, J = 8.3, 6.7 Hz, 1H), 1.43-1.08 (m, 4H), 0.82 (t, J = 7.0 Hz, 3H). |
| 9 | (−)-4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one | 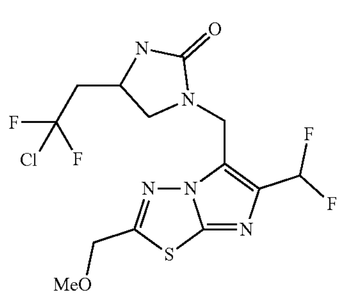 [SMILES: COCc1nn2c(CN3CC(CC(F)(F)Cl)NC3=O)c(C(F)F)nc2s1] | 416.0 | 6.84 (t, J = 54.5 Hz, 1H), 4.79 (d, J = 31.3 Hz, 5H), 4.03 (dt, J = 12.1, 6.1 Hz, 1H), 3.60 (t, J = 8.8 Hz, 1H), 3.52 (s, 3H), 3.08 (dd, J = 9.0, 7.2 Hz, 1H), 2.65-2.42 (m, 2H) |

TABLE 1-continued

Physical Characterization of Example Compounds.

| no | Compound NAME | Structure | MH+ | $^1$H NMR δ (DMSO-$d_6$) |
|---|---|---|---|---|
| 10 | (+)-4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one | 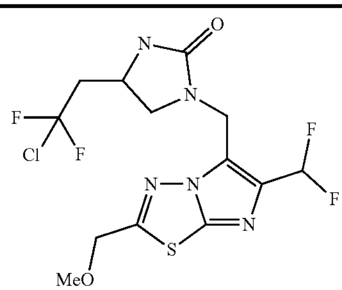 | 416.0 | 6.84 (t, J = 54.5 Hz, 1H), 4.79 (d, J = 31.3 Hz, 5H), 4.03 (dt, J = 12.1, 6.1 Hz, 1H), 3.60 (t, J = 8.8 Hz, 1H), 3.52 (s, 3H), 3.08 (dd, J = 9.0, 7.2 Hz, 1H), 2.65-2.42 (m, 2H) |
| 11 | (+)-1-[[6-(difluoromethyl)-2-(methoxymethyl)imidazo[2,1-b][1,3,4]thiadiazol-5-yl]methyl]-4-(2,2-difluoropropyl)imidazolidin-2-one | 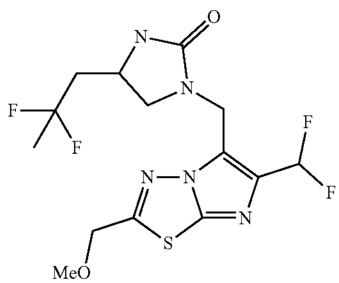 [SMILES: COCc1nn2c(CN3CC(CC(C)(F)F)NC3=O)c(C(F)F)nc2s1] | 396.0 | 7.13 (t, J = 53.4 Hz, 1H), 6.65 (s, 1H), 4.82 (s, 2H), 4.73-4.47 (m, 2H), 3.74 (t, J = 7.2 Hz, 1H), 3.43 (s, 4H), 2.99 (t, J = 8.1 Hz, 1H), 2.07 (td, J = 17.5, 17.0, 6.4 Hz, 2H), 1.59 (t, J = 19.3 Hz, 3H). |
| 12 | (−)-1-[[6-(difluoromethyl)-2-(methoxymethyl)imidazo[2,1-b][1,3,4]thiadiazol-5-yl]methyl]-4-(2,2-difluoropropyl)imidazolidin-2-one | 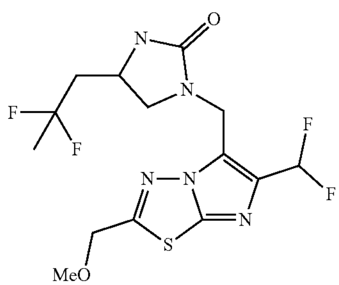 [SMILES: COCc1nn2c(CN3CC(CC(C)(F)F)NC3=O)c(C(F)F)nc2s1] | 396.0 | 7.13 (t, J = 53.4 Hz, 1H), 6.65 (s, 1H), 4.82 (s, 2H), 4.73-4.47 (m, 2H), 3.74 (t, J = 7.2 Hz, 1H), 3.43 (s, 4H), 2.99 (t, J = 8.1 Hz, 1H), 2.07 (td, J = 17.5, 17.0, 6.4 Hz, 2H), 1.59 (t, J = 19.3 Hz, 3H). |
| 13 | (+)-5,5-dideuterio-1-[[6-(difluoromethyl)-2-(methoxymethyl)imidazo[2,1-b][1,3,4]thiadiazol-5-yl]methyl]-4-propyl-imidazolidin-2-one | 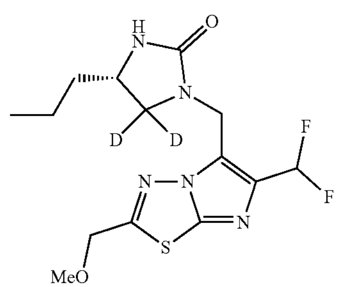 [SMILES: [2H]C1([2H])[C@H](CCC)NC(=O)N1Cc1c(C(F)F)nc2sc(COC)nn12] | 362.1 | |
| 14 | (−)-5,5-dideuterio-1-[[6-(difluoromethyl)-2-(methoxymethyl)imidazo[2,1-b][1,3,4]thiadiazol-5-yl]methyl]-4-propyl-imidazolidin-2-one | 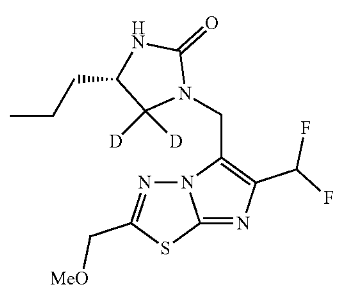 [SMILES: [2H]C1([2H])[C@H](CCC)NC(=O)N1Cc1c(C(F)F)nc2sc(COC)nn12] | 362.1 | |

Example 8. Binding Assays to SV2A and SV2C

Human SV2A and SV2C proteins were expressed in human embryonic kidney (HEK) cells. HEK SV2A and HEK SV2C membrane preparations were prepared as described in Gillard et al (Eur. J. Pharmacol. 2006, 536, 102-108). To measure affinity of non-labelled compounds, competition experiments were performed as follow: Membranes expressing SV2 proteins (5 to 15 μg proteins per assay) were incubated for 60 min at 37° C. with either

[³H]-2-[4-(3-azidophenyl)-2-oxo-1-pyrrolidinyl] butanamide (5 nM) and/or [³H]-4R-(2-chloro-2,2-difluoroethyl)-1-{[2-(methoxymethyl)-6-(trifluoromethyl)imidazo[2,1-b][1,3,4]thiadiazol-5-yl]methyl}pyrrolidin-2-one (25 nM) in 0.2 ml of a 50 mM Tris-HCl buffer (pH 7.4) containing 2 mM $MgCl_2$, 0.1% dimethylsulfoxide and ten increasing concentrations of non-labelled test compound (0.1 nM to 10 µM). At the end of the incubation period, the membrane-bound radioligand was recovered by rapid filtration through GF/C glass fiber filters pre-soaked in 0.1% polyethyleneimine. Membranes were washed with at least 4 times the assay volume of ice-cold 50 mM Tris HCl buffer (pH 7.4). The filters were dried and the radioactivity determined by liquid scintillation. The entire filtration step did not exceed 10 sec. Measured affinity $pIC_{50}$ values were corrected to pKi according to Cheng and Prusoff (Biochem. Pharmacol. 1973, 22(23), 3099-3108).

Compounds of formula (I) according to the invention typically show pKi SV2A values of at least 6.5. and pKi SV2C values of at least 6.0.

Example 9. Seizure Models

Male NMRI mice (Charles River, Germany) weighing 22-32 g are used in all experiments. The animals are kept on a 12/12-h light/dark cycle with lights on at 6:00 am and are housed at a temperature maintained at 20-21° C. and at humidity of about 40%. The mice are housed in groups of 10 per cage (Type III). All animals have free access to standard pellet food and water before random assignment to experimental groups consisting of 10 mice each. All animal experiments are done according to the National Rules on Animal Experiments and conducted in accordance with the guidelines of the European Community Council directive 2010/63/EU. A local ethical committee approved the experimental protocols.

9.1 6 Hz Seizure Model

The 6 Hz model is carried out according to a previously described protocol (Kaminski et al., Epilepsia (2004), 45, 864-867). Briefly, corneal stimulation (44 mA, 0.2 ms-duration monopolar rectangular pulses at 6 Hz for 3 s) is delivered by a constant-current device (ECT Unit 57800; Ugo Basile, Comerio, Italy). A drop of 0.4% oxybuprocaine hydrochloride (Unicaine, Thea, France) is placed on the eyes before electrical stimulation. During the stimulation, mice are manually restrained and released into the observation cage (38×26×14 cm) immediately after the current application. The seizures are often preceded by a brief period (~2-3 s) of intense locomotor agitation (wild running and jumping). The animals then exhibit a "stunned" posture associated with rearing, forelimb automatic movements and clonus, twitching of the vibrissae, and Strub-tail. At the end of the seizure, animals resume their normal exploratory behavior. The experimental endpoint is protection against the seizure. The animal is considered to be protected if it resumes its normal exploratory behavior within 7 s from the stimulation.

In vivo activities determined for test compounds are typically comprised between 0.05 mg/kg and 10 mg/kg after single IP dosing.

9.2 Pentylenetetrazol (PTZ) Seizure Model

Pentylenetetrazol is used at the previously established $CD_{97}$ dose of 89 mg/kg; a convulsive dose inducing clonic convulsions of all four extremities in 97% of mice (Klitgaard et al., Eur. J. Pharmacol. (1998), 353, 191-206). Immediately following pentylenetetrazol injection the mice are placed individually in Perspex cages and observed for the presence of clonic convulsions in all four extremities and tonic hindlimb extension during 60 min period.

In vivo activities determined for test compounds are typically comprised between 0.5 mg/kg and 30 mg/kg after single IP dosing.

Example 10. Azamulin Assay

Cryopreserved human hepatocytes (pool of 20 donors, BSU batch from Celsis/IVT/Bioreclamation) were thawed accordingly the provider's information. Viability (trypan blue exclusion) was higher than 75%. Pre-incubations (250 µL of hepatocytes suspension at $2 \times 10^6$ hepatocytes/mL) were carried out with William's medium, containing 2 mM of glutamine and 15 mM of Hepes, in 48-well plates at +37° C., in an incubator (5% $CO_2$), under gentle agitation (vibrating agitator, Titramax 100, ca 300 rpm) during 30 min. After the pre-incubation, the incubation was initiated by adding to hepatocytes, 250 µL of culture medium (see composition above) containing UCB compound (1 µM) or midazolam (positive control) with or without azamulin (6 µM-specific CYP3A4/5 inhibitor). Final concentrations of UCB compound and azamulin in the incubates are 0.5 µM and 3 µM, respectively. The cell suspensions was rapidly re-homogenized by 2 in-out pipetting. After 0, 30, 60, 120, 180 and 240 minutes of incubation, reactions were stopped by transferring 50 µl of incubates into the appropriate well from 96-well plate containing 50 µL of ice cold acetonitrile with ketoconazole 1 µM as internal standard. Before each sampling, cell incubates are re-homogenized by 2 in out pipetting.

Once the incubation is finished, 96-well plates are centrifuged at ca 3700 rpm, +4° C., for 15 minutes. 50 µL of supernatants are transferred into the wells of other deep well plates to which 150 µL of $H_2O$ Millipore were added. These samples were are analyzed by micro UPLC/HR-MS for parent disappearance and monitoring of metabolite formation.

The CYP3A4/5 contribution known as fraction metabolized by CYP3A4/5 ($f_{m,CYP3A4/5}$) was calculated for each compound from the ratio between CLint (based on parent drug disappearance) in absence and in presence of azamulin, by using the following equation:

$$Fm_{CYP3A4/5} = 1 - \frac{CL_{int\,with\,azamulin}}{CL_{int\,without\,azamulin}}$$

The fraction metabolized by CYP3A4/5 ($f_{m,CYP3A4/5}$) of test compounds are typically comprised between 0 and 40%.

The invention claimed is:

1. A compound having formula (I), or a geometrical isomers, enantiomers, diastereomers, isotopes or mixtures thereof, or a pharmaceutically acceptable salt thereof,

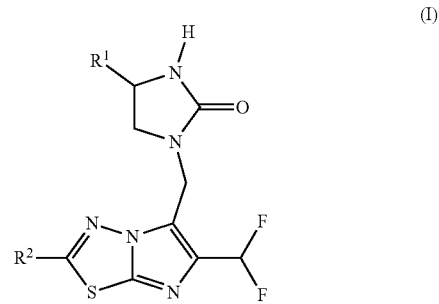

wherein
R¹ is a $C_{1-4}$ alkyl optionally substituted by one or more halogen substituents;
R² is a $C_{1-4}$ alkyl substituted by an alkoxy substituent.

2. A compound according to claim 1, wherein R¹ is an i-butyl, a n-propyl, a 2,2-difluoropropyl, a 2-chloro-2,2-difluoroethyl, a 2,2-difluoroethyl, a 2,2,2-trifluoroethyl, or a 2-fluoroethyl moiety.

3. A compound according to claim 1, wherein R¹ is n-propyl, a 2-chloro-2,2-difluoroethyl, a 2,2-difluoropropyl or a 2,2,2-trifluoroethyl moiety.

4. A compound according to claim 1, wherein R² is a methoxymethyl, a [($^2$H$_3$)methyloxy]methyl, a methoxy($^2$H$_2$)methyl, or a [($^2$H$_3$)methyloxy]($^2$H$_2$)methyl moiety.

5. A compound according to claim 1, wherein:
R¹ is a n-propyl or a 2,2,2-trifluoroethyl moiety;
R² is a methoxymethyl, a methoxy($^2$H$_2$)methyl, a [($^2$H$_3$)methyloxy]methyl or a [($^2$H$_3$)methyloxy]($^2$H$_2$)methyl moiety.

6. A compound according to claim 1 which is:
(4S)-1-[[6-(difluoromethyl)-2-(methoxymethyl)imidazo[2,1-b][1,3,4]thiadiazol-5-yl]methyl]-4-propyl-imidazolidin-2-one;
(4R)-1-[[6-(difluoromethyl)-2-(methoxymethyl)imidazo[2,1-b][1,3,4]thiadiazol-5-yl]ethyl]-4-propyl-imidazolidin-2-one;
(+)-4-1-[[6-(difluoromethyl)-2-(methoxymethyl)imidazo[2,1-b][1,3,4]thiadiazol-5-yl]methyl]-4-(2,2,2-trifluoroethyl)imidazolidin-2-one;
(−)-4-1-[[6-(difluoromethyl)-2-(methoxymethyl)imidazo[2,1-b][1,3,4]thiadiazol-5-yl]methyl]-4-(2,2,2-trifluoroethyl)imidazolidin-2-one;
(4S)-1-[[2-[dideuterio(trideuteriomethoxy)methyl]-6-(difluoromethyl)imidazo[2,1-b][1,3,4]thiadiazol-5-yl]methyl]-4-propyl-imidazolidin-2-one;
(4R)-1-[[2-[dideuterio(trideuteriomethoxy)methyl]-6-(difluoromethyl)imidazo[2,1-b][1,3,4]thiadiazol-5-yl]methyl]-4-propyl-imidazolidin-2-one;
(4S)-1-[[2-[dideuterio(methoxy)methyl]-6-(difluoromethyl)imidazo[2,1-b][1,3,4]thiadiazol-5-yl]methyl]-4-propyl-imidazolidin-2-one;
(4R)-1-[[2-[dideuterio(methoxy)methyl]-6-(difluoromethyl)imidazo[2,1-b][1,3,4]thiadiazol-5-yl]methyl]-4-propyl-imidazolidin-2-one;
(−)-4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one;
(+)-4-(2-chloro-2,2-difluoro-ethyl)-1-[[6-(difluoromethyl)-2-(methoxymethyl)imidazo[2,1-b][1,3,4]thiadiazol-5-yl]methyl]imidazolidin-2-one;
(+)-1-[[6-(difluoromethyl)-2-(methoxymethyl)imidazo[2,1-b][1,3,4]thiadiazol-5-yl]methyl]-4-(2,2-difluoropropyl)imidazolidin-2-one;
(−) 1-[[6-(difluorornethyl)-2-(methoxymethyl)imidazo[2,1-b][1,3,4]thiadiazol-5-yl]methyl]-4-(2,2-difluoropropyl)imidazolidin-2-one;
(+)-5,5-dideuterio-1-[[6-(difluoromethyl)-2-(methoxymethyl)imidazo[2,1-b][1,3,4]thiadiazol-5-yl]methyl]-4-propyl-imidazolidin-2-one; or
(−)-5,5-dideuterio-1-[[6-(difluoromethyl)-2-(methoxymethyl)imidazo[2,1-b][1,3,4]thiadiazol-5-yl]methyl]-4-propyl-imidazolidin-2-one.

7. A pharmaceutical composition comprising an effective amount of a compound according to claim 1 in combination with a pharmaceutically acceptable diluent or carrier.

8. A method for the treatment of epilepsy, epileptogenesis, seizure disorders, or convulsions, comprising administering to a patient in need thereof an effective amount of a compound or salt according to claim 1.

9. A method according to claim 8, wherein the treatment is for refractory seizures.

10. A compound according to claim 2, wherein R² is a methoxymethyl, a [($^2$H$_3$)methyloxy]methyl, a methoxy($^2$H$_2$)methyl, or a [($^2$H$_3$)methyloxy]($^2$H$_2$)methyl moiety.

11. A compound according to claim 4, wherein:
R¹ is a n-propyl or a 2,2,2-trifluoroethyl moiety;
R² is a methoxymethyl, a methoxy($^2$H$_2$)methyl, a [($^2$H$_3$)methyloxy]methyl or a [($^2$H$_3$)methyloxy]($^2$H$_2$)methyl moiety.

* * * * *